US007641592B2

(12) United States Patent
Roche

(10) Patent No.: US 7,641,592 B2
(45) Date of Patent: Jan. 5, 2010

(54) INTERVAL FITNESS TRAINING

(75) Inventor: Jonathan D. Roche, Erie, CO (US)

(73) Assignee: Jonathan Roche Ventures, LLC, Broomfield, CO (US)

( * ) Notice: Subject to any disclaimer, the term of this patent is extended or adjusted under 35 U.S.C. 154(b) by 301 days.

(21) Appl. No.: 11/430,390

(22) Filed: May 8, 2006

(65) Prior Publication Data

US 2006/0250524 A1 Nov. 9, 2006

Related U.S. Application Data

(60) Provisional application No. 60/678,347, filed on May 6, 2005.

(51) Int. Cl.
*A63B 71/00* (2006.01)
*A63B 69/00* (2006.01)
(52) U.S. Cl. .......................................... 482/9; 434/247
(58) Field of Classification Search ................ 482/1–9; 434/236, 238, 247; 715/961
See application file for complete search history.

(56) References Cited

U.S. PATENT DOCUMENTS

| | | | | | |
|---|---|---|---|---|---|
| 5,803,870 | A | * | 9/1998 | Buhler .............................. | 482/8 |
| 5,879,270 | A | * | 3/1999 | Huish et al. ..................... | 482/8 |
| 5,890,997 | A | * | 4/1999 | Roth ................................ | 482/8 |
| 5,976,083 | A | * | 11/1999 | Richardson et al. ............ | 600/300 |
| 6,450,922 | B1 | * | 9/2002 | Henderson et al. .............. | 482/8 |
| 6,478,736 | B1 | * | 11/2002 | Mault ............................. | 600/300 |
| 6,554,776 | B1 | * | 4/2003 | Snow et al. ..................... | 600/532 |
| 6,687,535 | B2 | * | 2/2004 | Hautala et al. .................. | 600/520 |
| 6,716,139 | B1 | * | 4/2004 | Hosseinzadeh-Dolkhani et al. ................................ | 482/1 |
| 6,740,007 | B2 | * | 5/2004 | Gordon et al. .................. | 482/9 |
| 6,945,911 | B2 | * | 9/2005 | Jackowski ....................... | 482/9 |
| 7,063,643 | B2 | * | 6/2006 | Arai ................................ | 482/8 |
| 7,063,644 | B2 | * | 6/2006 | Albert et al. .................... | 482/8 |
| 7,070,539 | B2 | * | 7/2006 | Brown et al. .................... | 482/8 |
| 7,115,076 | B2 | * | 10/2006 | Oglesby et al. ................. | 482/54 |
| 7,128,693 | B2 | * | 10/2006 | Brown et al. .................... | 482/8 |
| 7,435,203 | B2 | * | 10/2008 | Anderson et al. ............... | 482/52 |
| 2002/0086774 | A1 | * | 7/2002 | Warner ........................... | 482/8 |
| 2002/0107433 | A1 | * | 8/2002 | Mault ............................. | 600/300 |
| 2003/0017913 | A1 | * | 1/2003 | Stewart .......................... | 482/8 |
| 2003/0017914 | A1 | * | 1/2003 | Jackowski ....................... | 482/9 |
| 2003/0027688 | A1 | * | 2/2003 | Gordon et al. .................. | 482/9 |
| 2004/0029684 | A1 | * | 2/2004 | Zarif ............................... | 482/8 |

(Continued)

OTHER PUBLICATIONS

Hulens, M., G. Vansant, R. Lysens, A.L. Claessens, and E. Muls. "Exercise capacity in lean versus obese women." Scandanavian Journal of Medicine & Sience in Sports 11 (2001): 305-09.*

(Continued)

*Primary Examiner*—Loan H Thanh
*Assistant Examiner*—Sandhara M Ganesan
(74) *Attorney, Agent, or Firm*—Peter B. Scull; Kristina M. Kalan; Berenbaum Weinshienk PC

(57) ABSTRACT

A computer-implemented method and/or computer program product for developing a physical fitness regimen, including establishing individualized physical fitness parameters based upon individualized information; obtaining physical fitness data from one or more computer database sources; developing a physical fitness regimen based upon the individualized information and the physical fitness data.

20 Claims, 30 Drawing Sheets

U.S. PATENT DOCUMENTS

2004/0077462 A1* 4/2004 Brown et al. .................. 482/8
2004/0198555 A1* 10/2004 Anderson et al. ............. 482/8
2004/0229729 A1* 11/2004 Albert et al. .................. 482/8
2005/0090372 A1* 4/2005 Burrows et al. ............... 482/8
2005/0107216 A1* 5/2005 Lee et al. ...................... 482/8
2005/0164833 A1* 7/2005 Florio ........................... 482/9
2005/0202934 A1* 9/2005 Olrik et al. .................... 482/8

OTHER PUBLICATIONS

Westcott, Wayne. "Interval Training." Personal Excellence 9 (2004): 14-14.*

* cited by examiner

FIG. 4

☐ Have you had a mother, sister, or daughter suffer a heart attack, coronary bypass or sudden death before the age of 65?

Section-2

☐ Are you a current smoker of have you quit within the last 6 months?

Section-3

☐ Do you have a systolic blood pressure of greater than or equal to 140 or a diastolic blood pressure of greater than or equal to 90, confirmed at least two times?

☐ You don't know your blood pressure levels?

☐ Are you taking any blood pressure medications?

Section-4

☐ Do you have a total blood cholesterol level of greater than 200 and/or an HDL level of less than 35?

☐ Are you taking any cholesterol medications?

☐ Is your LDL level greater than 130 mg/dL?

☐ You don't know your cholesterol levels?

Section-5

☐ Is your fasting blood glucose level greater than or equal to 110 mg/dL, confirmed on at least two occasions?

☐ You don't know your fasting blood glucose level?

Section-6

☐ Is your waist circumference greater than 39 inches?

☐ You don't know your waist circumference?

Section-7

☐ Do you get fewer than 30 minutes (accumulated time) of moderate-intensity (equivalent to a brisk walk) exercise most days of the week?

Section-8

☐ Is your HDL cholesterol level greater than 60 mg/dL?

[Next]   [Cancel]

"It's a speed bump, not a road block"

Q&A'S

Welcome to our Q&A section. We are here to answer all of your questions about the Momentum Weight Loss System. Remember that life-long, sustainable, and healthy weight loss is a combination of both exercise and nutrition.

I have a question about:

I. Weight Loss
II. Interval Workouts
III. Nutrition

I. Weight Loss Questions:

(Remember, weight loss is a balance between exercise and nutrition. Be sure to read all of the questions and answers in this section to understand how these two work together, and how you can take control of your weight loss goals.)

I-A: What is "healthy" weight loss, and how much should I expect to lose on this program?
I-B: How important is hydration to weight loss?
I-C: How much should I be eating? How can I know if I'm eating too much or too little?
I-D: I am not losing as much as I had hoped to. Should I be doing something differently?
I-E: What other types of workouts can I do to kick in the weight loss?

II. Interval Workout Questions:     Back To Top (Remember, weight loss is a balance between exercise and nutrition. Be sure to read all of the questions and answers in this section to understand how these two work together, and how you can take control of your weight loss goals.)

II-A: What is anaerobic threshold (AT)?
II-B: Why it is important to exercise based on my AT?
II-C: Should I stay consistent with the Workout Schedules' mix of the 2-, 3-, and 4-minute intervals, or can I pick my favorite one and stick to that?
II-D: Can I do more than three intervals a week?
II-E: Some days I hit AT and can sustain it. Other days, I barely reach it. Why is this? How long do I need to maintain the target heart rate for it to "count" as an interval workout day?

FIG. 23

Fig. 26

INTERVAL FITNESS TRAINING

CROSS-REFERENCE TO RELATED APPLICATIONS

The present invention claims the benefit of and priority from the prior-filed U.S. Provisional Patent Application, No. 60/678,347; filed May 6, 2005, entitled "Interval Fitness Traninig;" the subject matter of which hereby being specifically incorporated herein by reference for all that it discloses and teaches.

BACKGROUND

The present disclosure relates generally to physical fitness training, and more particularly to the development and management of individualized training regimens.

Overall body fitness is a well-recognized attribute for human health. However, fad diets, expensive eating plans, fitness machines and workout routines at an exercise center or gym are not always or uniformly sufficient. Improved alternatives are thus desired.

SUMMARY

Implementations described and claimed herein address the foregoing and other situations by providing a system, product and/or methodology for optimizing individualized training or maximizing weight loss by coupling heart rate-based training with customized interval workouts. This system may offer users of many types, regardless of age, fitness level, and exercise preference, affordable access to their own personal trainer-in-a-box. In one implementation, the system may include instructional DVDs, web-based software and online support, a nutritional guide, a heart rate monitor, and/or a workout log.

In a systematic or methodological implementation, the users may be provided a computer-based program, accessible either via personal computer or via the internet. The users may then access the software and use this to set up a personalized workout program to track workouts and weight loss. Because the program is based on heart rate-based training and intervals (increasing and decreasing your exertion during workouts) people can do them in the gym or on a walk around the block. As users chart their progress, instructors may be used to provide online support, instruction, and accountability. A nutrition program may also be included. Then, by following the workout and nutrition program, users can achieve better fitness and/or safe weight loss results (approximately one to two pounds per week) in three focused workouts a week, while strengthening the hearts and lungs.

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following more particular written Detailed Description of various embodiments and implementations as further illustrated in the accompanying drawings and defined in the appended claims.

BRIEF DESCRIPTION OF DRAWINGS

In the drawings:

FIG. 4 is still another user interface screen which may be used herewith;

FIG. 6 is a further user interface screen which may be used herewith;

FIG. 8 is yet still a further user interface screen which may be used herewith;

FIG. 15 is yet still another user interface screen which may be used herewith;

FIG. 23 is still one further user interface screen which may be used herewith;

FIG. 26 is still one further user interface screen which may be used herewith;

DETAILED DESCRIPTION

Figure 1:
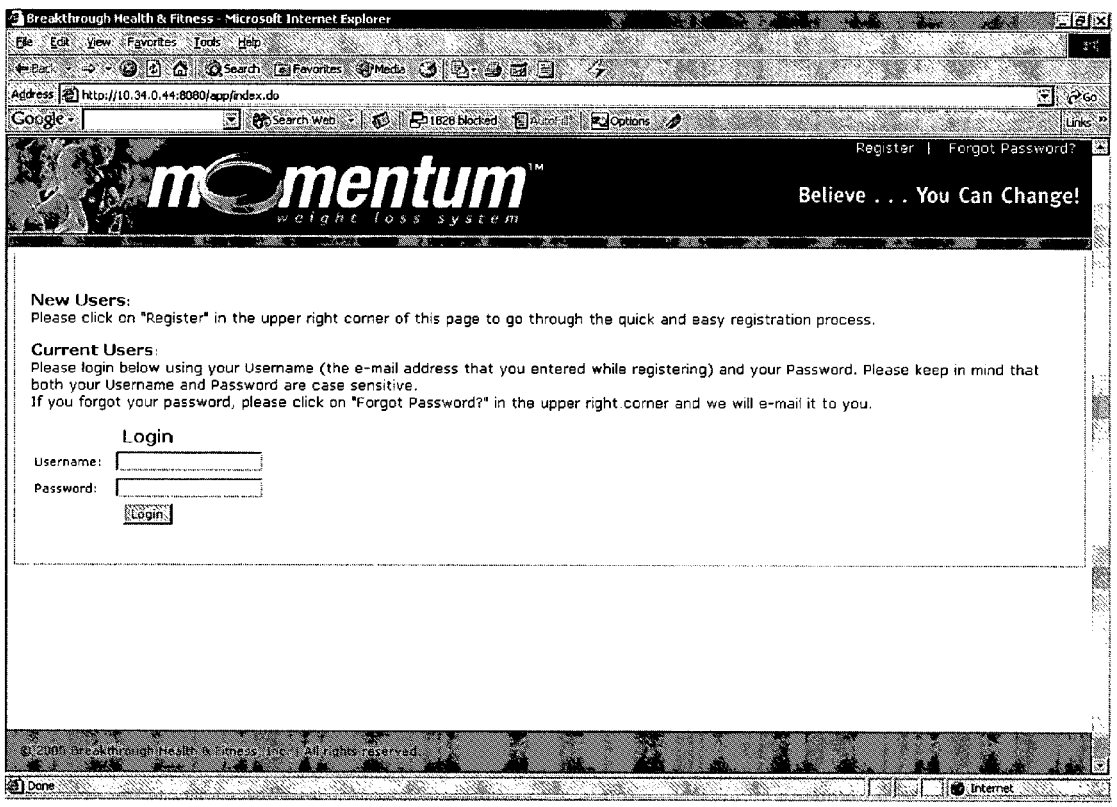
FIG. 1 is a user interface screen which may be used herewith.
Figure 2:
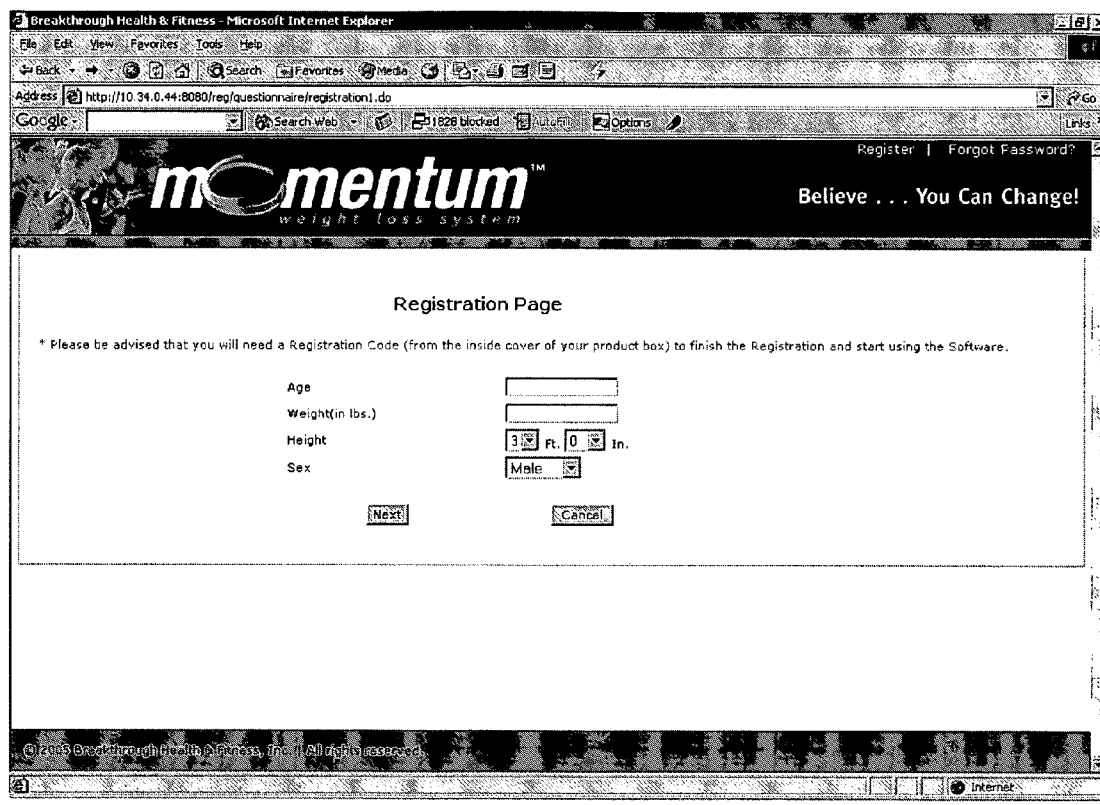
FIG. 2 is another user interface screen which may be used herewith.

Herein described is technology which may be in the form of a methodology, system or tool for people to use to create customized heart rate based interval training plans. With this tool the user may be able to answer a questionnaire (e.g., fill out a form) with a series of questions in a short time period (in one example, on the order of less than 5 minutes or so) that would then be used by the tool to set the user up on a highly effective and customized fitness plan. Moreover, the tool can be used to track workouts and weight loss.

The tool hereof may be, include, or be a part of a system, method and/or software and/or it may include or provide apparatus features. An example of an apparatus hereof is a distributed product, as for example in a box, which may include one or more of a software program on disc (e.g., a CD), a heart rate monitor, nutrition and lifestyle materials, one or more workout digital video discs (DVDs) and/or motivational compact discs (CDs).

Methodologically, the tool can be software based (though need not be), and can reside locally on, for example, a personal computer, or may be accessed via the internet with distributed databases and/or applications.

In more detail in at least one implementation, the user instructions may be as follows, noting first that there may be four Major Sections to the program: namely, 1) Workout Schedule; 2) Weight Tracker; 3) Workout Log; and, 4) My Info.

For the Workout Schedule section; there may be two sub-section areas: e.g., a "Workout List" and a "Post-Workout Questionnaire". See e.g., FIGS. 13-16 of the detailed example described further below.

The Workout List sub-section (see e.g., FIGS. 13, 14 and 15, described further below) of the Workout Schedule may list a user's Weekly Workout Schedule. Also, in an implementation, the User's Anaerobic Threshold (AT) may be listed (e.g., at the top). In simple terms, the user's AT may be defined as the heart rate at which the user shifts from a conversational to a non-conversational speed; i.e., from being able to talk to having trouble talking. In medical terms, this may be the heart rate at which lactic acid starts to accumulate in the user's muscle stream. The user's training plan may be formed based on the user's AT to help the user maximize the user's cardio and weight loss results. This page may also show the user's Days, Exercise, Lower and Upper Limit Target Heart Rates, Lower and Upper Limit Actual Numbers and Approximate Time. The user can click on the actual workout under Exercise and the user will see the detailed Workout for that day.

The user may also be provided with a Post-Workout Questionnaire (see FIG. 16 described further below) of the Workout Schedule section on which the user may click after completing a workout, preferably after completing one or two Interval Workouts. The user's answers to the two questions (see below) will help in figuring out if the user's Estimated AT is either too high, just right or too low. The user should keep filling out the Questionnaire after each workout until the user is feeling like the user is being tested but not crushed in the user's workouts. Once the user submits the user's answers to the two questions, the user will be asked to confirm the user's answers. Once the user does that, the software program may notify the user if the user's AT has been changed and will automatically update the user's Workout Schedule.

Note, in an implementation of a Workout Schedule section according hereto (see detailed EXAMPLE, below, including e.g., Table A), Interval Workouts may be the main component of the program/regimen hereof. Such workouts improve the user's recovery rates, strengthen the user's lungs and heart, maximize the user's calorie burning during the workout, and can leave the user's metabolism elevated for up to about 12 hours or more after each workout. In using Interval Workouts, the user may be thought to essentially be turning the his/her body into a Fat-Burning Machine. Interval Workouts are nothing more than shifting back and forth between pushing hard for a period, as for example three to five minutes, and then recovering for another period, e.g., one or two minutes. Often, this sort of cycle is repeated.

A first example is presented here of an Interval Workout useful herewith, such as one including four minutes On and two minutes Off. First, after warming up for five minutes, the regimen can be adapted to call for the user to workout and push up to a heart rate of 15 Below AT for the next four minutes. But the user is really not going to spend a full four minutes at that heart rate because it is going to take the user 60-90 seconds to get up to that heart rate, so that time is part of the four minutes. So at the four minutes mark (nine minutes overall) the user would then be directed by the regimen to recover for two minutes. This may include continuing to workout, but at a less strenuous level, such as having the user's Workout Schedule direct that the user's Target Heart Rate would now be 30 Below AT on the user's recoveries. Not, it may be that the user might only drop 8 or 10 beats or the user might drop 50. Either way, the user's recovery rates will improve over time. Keep in mind that in this example, the user is only recovering for two total minutes and the user will be starting the user's second interval at the eleven minute mark of the user's workout. So the user will follow this pattern until the user is done with the user's workout. Also keep in mind that the user will not be able to keep the user's heart rate at the exact target number, so it may be desirable that the user will be directed to keep within an envelope of ranges, such as by trying to keep it within a number of beats (e.g., three or more, or less) on either side of the user's Target Heart Rate.

Note also that cross training/non-interval training may also be incorporated in this systemology on off days, as for example Easy and/or Medium Cardio Day Cross-Training. Here, the user can do any exercise or activity that gets the user's heart rate up to between 30 Below AT and 10 Below AT. The user's goal should be to try to keep the user's Heart Rate in that zone for the specified time. The user would typically also be directed to make sure to Warm-Up for five minutes at the beginning and Cool Down for five minutes at the end.

The next Major Section which may be useful herewith may be a Weight Tracker which may also include two sub-section areas; namely, "Enter Weight" and "Graph". See e.g., FIGS. 17 and 18 of the detailed example described further below.

The Enter Weight sub-section may be adapted to allow the user enter the date and the user's current weight. The user would then enter the information and hit the "Add Weight" button (see FIG. 18 described further below). The Graph (see FIG. 17 described further below) would then update, in some implementations, automatically, with the user's new weight.

The Graph sub-section (FIG. 17) of the Weight Tracker may have the user's weight loss graphed out. The user can click on the "Graph" button to see this. The user's Goal Weight can be set up on the graph and the user can watch over time as the user may approach, i.e., get closer and closer to that goal weight.

A third Major Section introduced above and which may be useful herewith may be a Workout Log, which may also include two sub-section areas of the software/methodology; namely, a "Current Month" sub-section and a "Workout History" sub-section. See e.g., FIGS. 19 and 20 of the detailed example described further below.

The Current Month sub-section (FIG. 19, see below) may allow the user to enter the user's daily and weekly workouts. After selecting Save, the information may be tracked both in this sub-section and in the "Workout History" sub-section (FIG. 20, see below). This tool may serve to help the user look back and see how consistent the user has been with the user's workouts. Consistency is known to be a key part of weight loss success.

The Workout History sub-section (FIG. 20, see below) may provide for tracking some or all of the user's workouts since initially starting the program. The user's progress can be tracked for many purposes including psychological and/or motivational benefits as a result of any progresses shown in the results.

The My Info major section (see e.g., FIG. 21 of the detailed example described further below) of the software/methodology as introduced above may provide a variety of services. One may be for the user to change "The days the user will be able to exercise" and "How many minutes the user will be able to exercise on those days". The user's Full Name and Email Address may also be listed in this section, although it may, in many implementations be predetermined that the user will not be able to make changes to them for a variety of security and/or identification purposes. Indeed, it may be requested that the user continue to use the user's initial e-mail address as the user's Username even if the user changes these identifiers for other reasons.

EXAMPLE

In still further detail, an exemplar implementation of such general methodologies is shown in the attached drawings.

The first screenshot, FIG. 1, is a sample Login Page, which the user can see on first accessing the application. This Login Page can provide for handling various tasks, such as for example, the three tasks of registering, handling forgotten passwords and logging in. In more detail, these processes may be:

Register—Allows a new User to take a quick and Easy Registration Process.

Forgot Password—Allows an already registered user to fetch his forgotten password.

Login—Allows the registered user to log in to the application and use the system services.

Furthermore, the Register process may include a number of steps (such as for example, including a Risk Questionnaire, particularly a cardiovascular (CV) Risk Questionnaire and/or a Personal Details Section) to allow the user to get registered to the system. In many implementations, it may be recommended, if not required that before the user can go ahead with entering the system, in many instances even before they may enter any personal details they may need to go through a Risk Questionnaire, particularly, a CV Risk Questionnaire, see FIGS. 2, 3, 4, 5 and 6, that can determine the Risk Level of the User. Users can then be categorized as High Risk, Moderate Risk or Low Risk users and the master plans are assigned accordingly.

This CV Risk Questionnaire may then have the user enter a few details such as Age, Weight (in lbs.), select Height in Feet (Ft.) and Inches (In.) and Sex. The Age and Sex can be used to calculate the Risk Level of the user, i.e. If the User is Male>=45 years of age then he can be identified as Moderate Risk User or if the user is Female>=55 years of age then she can be identified as a Moderate Risk User. Furthermore, the Weight and Height can be used to calculate the BMI (body mass index of the user.):

BMI=Weight(Kg)/Height(in meter square)

This screen can also inform the user that the user may/should obtain a Registration Code (e.g., from the inside cover of the user's product box) to finish the Registration. After filling in valid and all minimum required data and clicking on Next button User can be taken to the next step of the CV risk Questionnaire, see FIG. 3, described below. Of course at any time, if the user chooses to click Cancel then the system may display a Message Page (e.g., a Cancel Page), see FIG. 24 described below.

Figure 3:
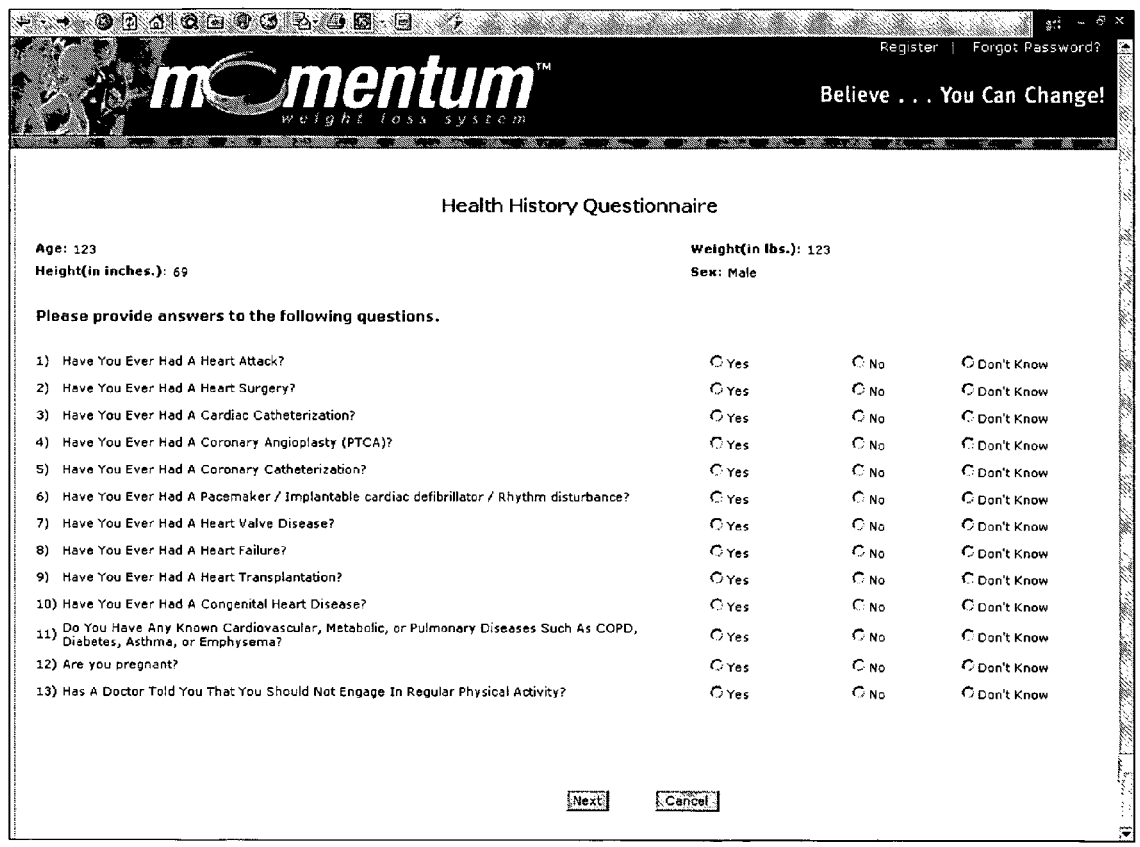
FIG. 3 is yet another user interface screen which may be used herewith.
Figure 24:
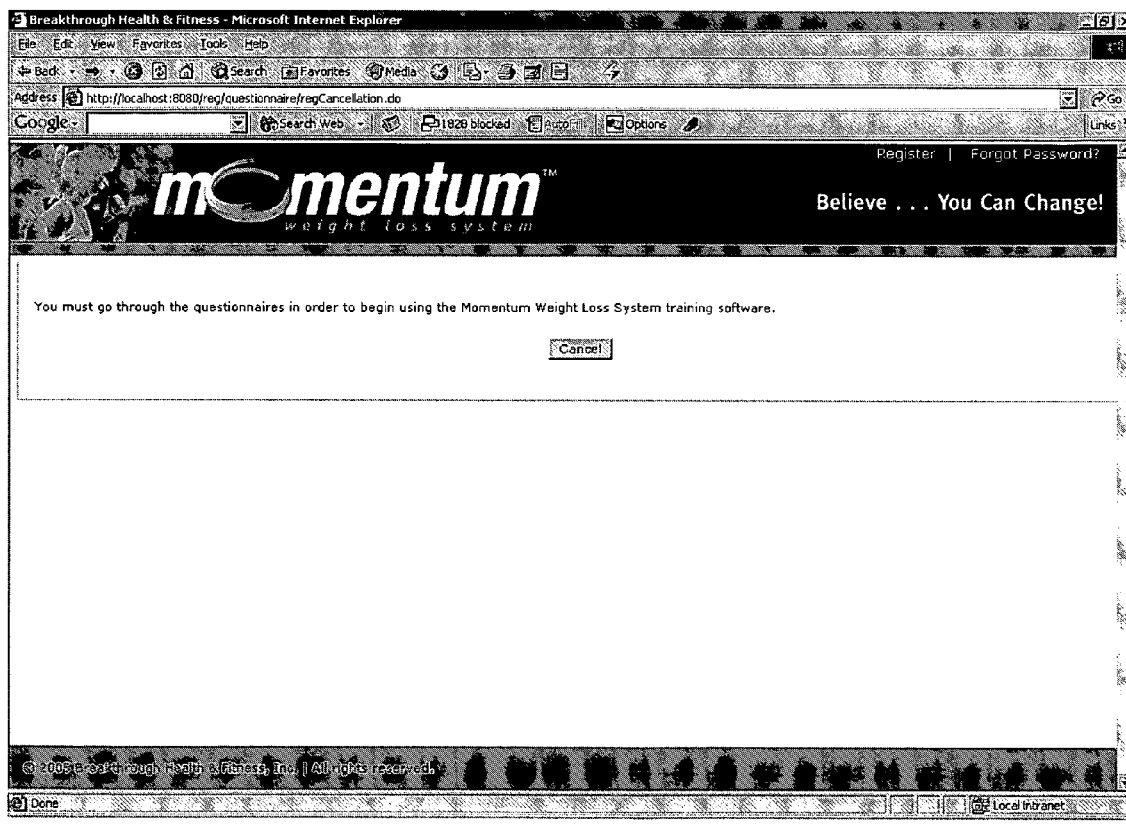
FIG. 24 is still one further user interface screen which may be used herewith; and, FIG. 25 is still one further user interface screen which may be used herewith.
Figure 25:
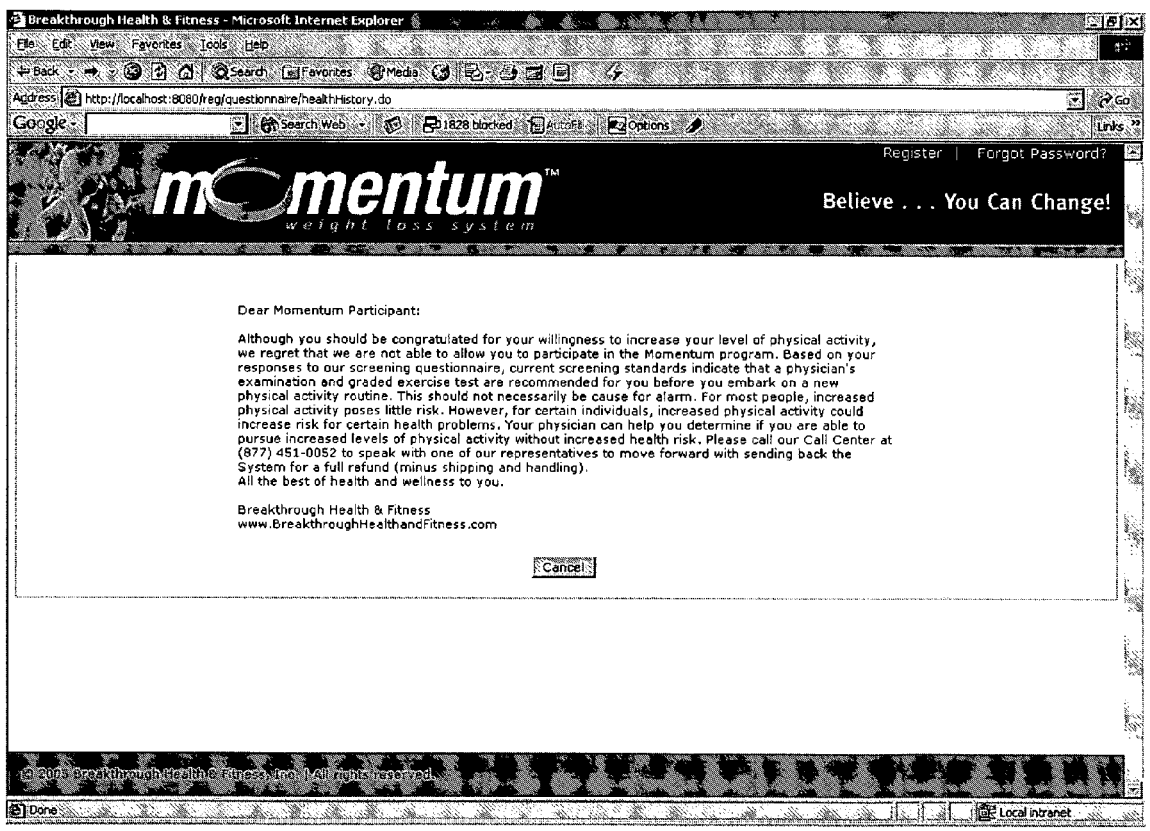

FIG. 3 presents an exemplar Health History Questionnaire (also the second screen of this exemplar CV Risk Questionnaire). As the name suggests this page may deal with some past health information of the user who wants to register. It may have a set of 13 questions each of which having three options Yes/No/Don't Know as Toggle buttons. In many implementations, a user can select only one of the three options and all questions are compulsory for the user to answer. This page can act as one of the determiners of whether the user is High Risk or not. On this screen, if the user selects "Yes" or "Don't Know" to any of the answers he may be identified as a High Risk User and may not be allowed to Register. But if the user selects to answer "No" to all the answers the user may then be taken forward to the next step of the CV Risk Questionnaire. As throughout, if the user chooses to click Cancel then the system displays a Message Page (e.g., a Cancel Page, see below) as shown in FIG. 24, e.g. If the user is identified as a High Risk User then the system displays a Refund Page (High Risk Refund Page, see below) as shown in FIG. 25.

Figure 4:
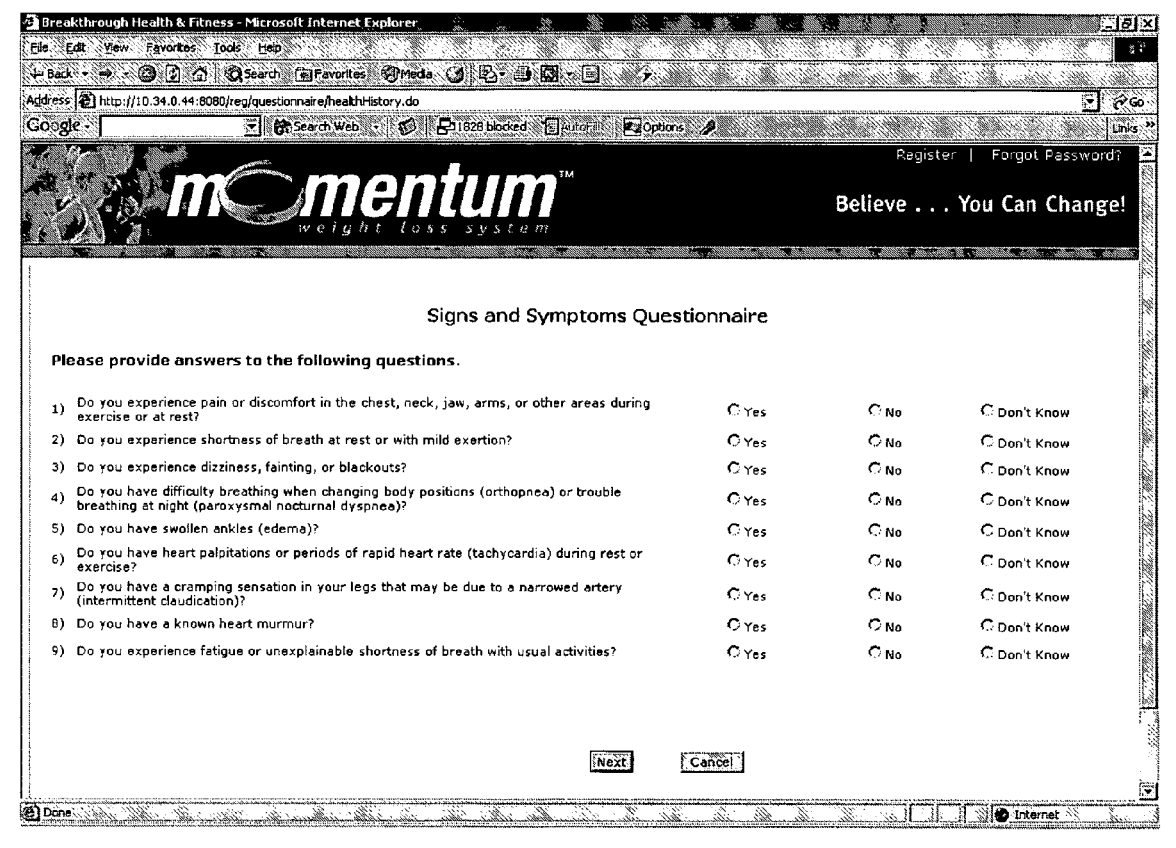

FIG. 4 presents an exemplar Signs and Symptoms Questionnaire (also the third screen of the CV Risk Questionnaire). As the name suggests this page may deal with some information on Signs and Symptoms of the user who wants to register. It may have, as shown, a set of nine questions each of which having a number of options, three options shown here, i.e., Yes/No/Don't Know as Toggle buttons. It may be preferred for the user to be able to select only one of the three options and may be desirable to make all questions compulsory for the user to answer. In this exemplar, this page can act as the final determiner of whether the user is High Risk or not. If the user selects "Yes" or "Don't Know" to any of the answers he may be identified as a High Risk User and may not be allowed to Register. But if the user selects to answer "No" to all the answers he is taken forward to the next step of the CV Risk Questionnaire. As before, if the user chooses to click Cancel then the system displays a Message Page (Cancel Page, see below) as shown in FIG. 24. If the user is identified as a High Risk User then the system displays a Refund Page (High Risk Refund Page, see below) as shown in FIG. 25.

Figure 5:
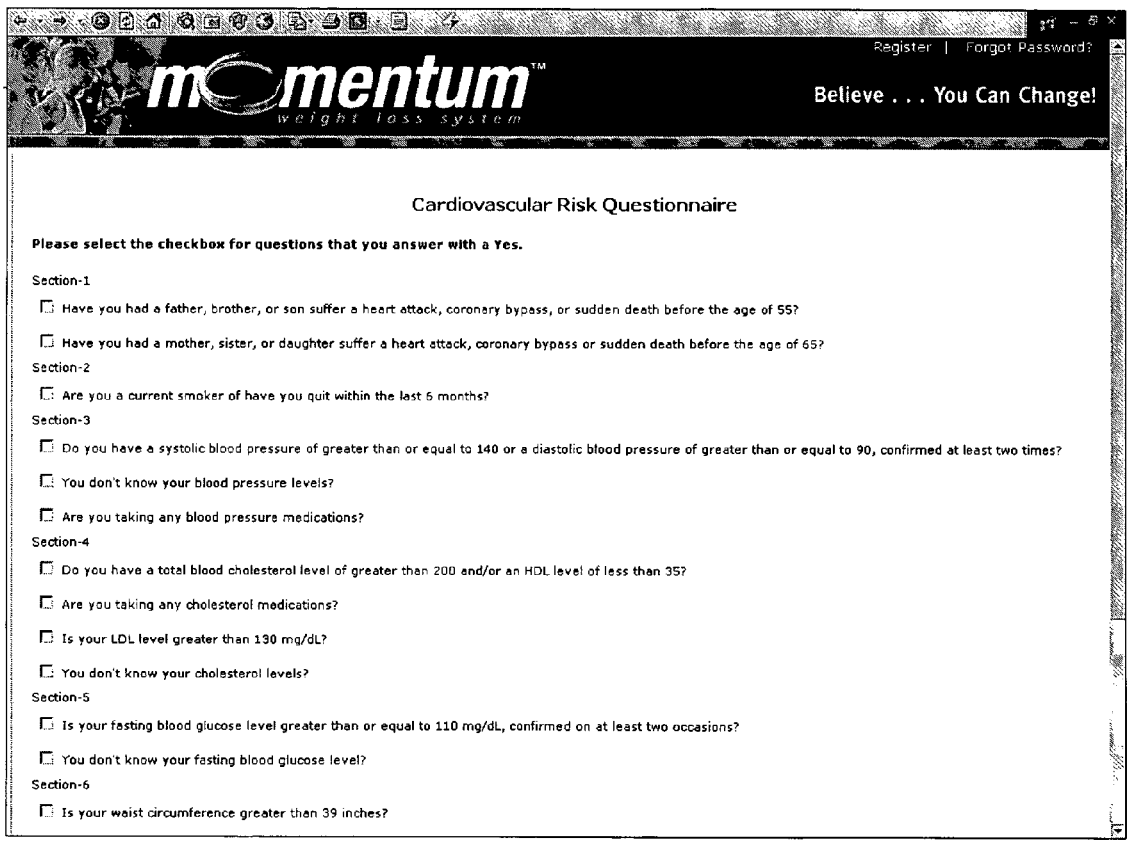
FIG. 5 is yet still another user interface screen which may be used herewith.

FIGS. 5 and 6 provide further exemplar Cardiovascular Risk Questionnaire questions (together making up the fourth screen of a CV Risk Questionnaire). As the name suggests these pages may provide the system with Cardio Related information of the user who wants to register. It may have a number of sections (this shown exemplar has 8 sections) of questions, with a check box corresponding to each question and here the questions are not mandatory. The user would be directed to mark the check box corresponding to the questions answered as a "Yes." Here the users may be classified as Moderate and/or Low Risk users. The logic for the same may be as follows. There is a counter maintained for risk, which gets incremented by one, on selection of even a single question in each section. But even if user answers more than one question in single section then also the counter is increased by one. One exception in the logic may be that if a user answers yes to a question in section 8 then the counter is decremented by one. If the user selects "Yes" or "Don't Know" to any of the answers he is identified as a High Risk User and is not allowed to Register. But if the user selects to answer "No" to all the answers he is taken forward to the next step of the CV Risk Questionnaire. As before, if the user chooses to click Cancel then the system displays a Message Page (Cancel Page, see below) as shown in FIG. 24.

Figure 7:
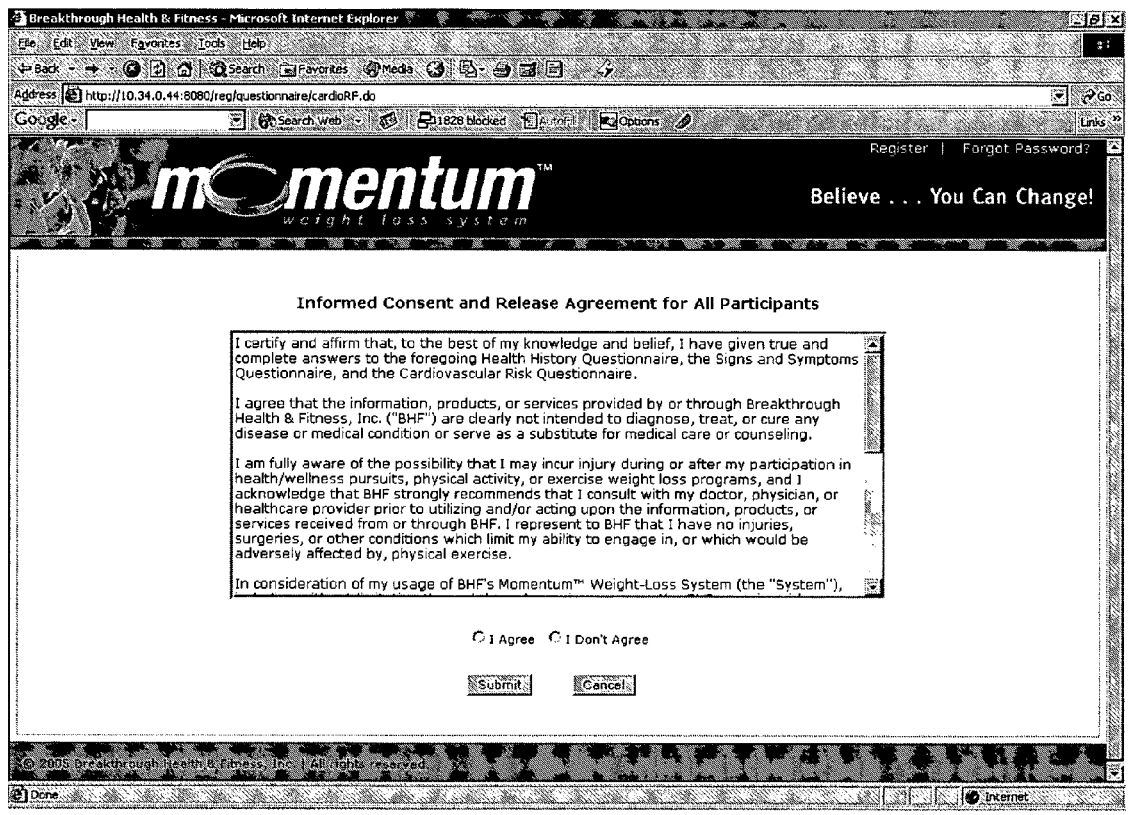
FIG. 7 is a still further user interface screen which may be used herewith.

FIG. 7 provides an exemplar Informed Consent and Release Agreement for All Participants (the fifth of the CV Risk Questionnaire Screens). Once the user has gone through all the Health Risk questions and his/her Risk Level is determined, the user would then be directed to the screen of FIG. 7 to toggle agreement to the form before moving ahead. Generally, in most implementations, the user would have to select "I Agree" to keep going on with the registration process. As before, if the user chooses to click Cancel then the system displays a Message Page (Cancel Page) as shown in FIG. 24.

Figure 8:
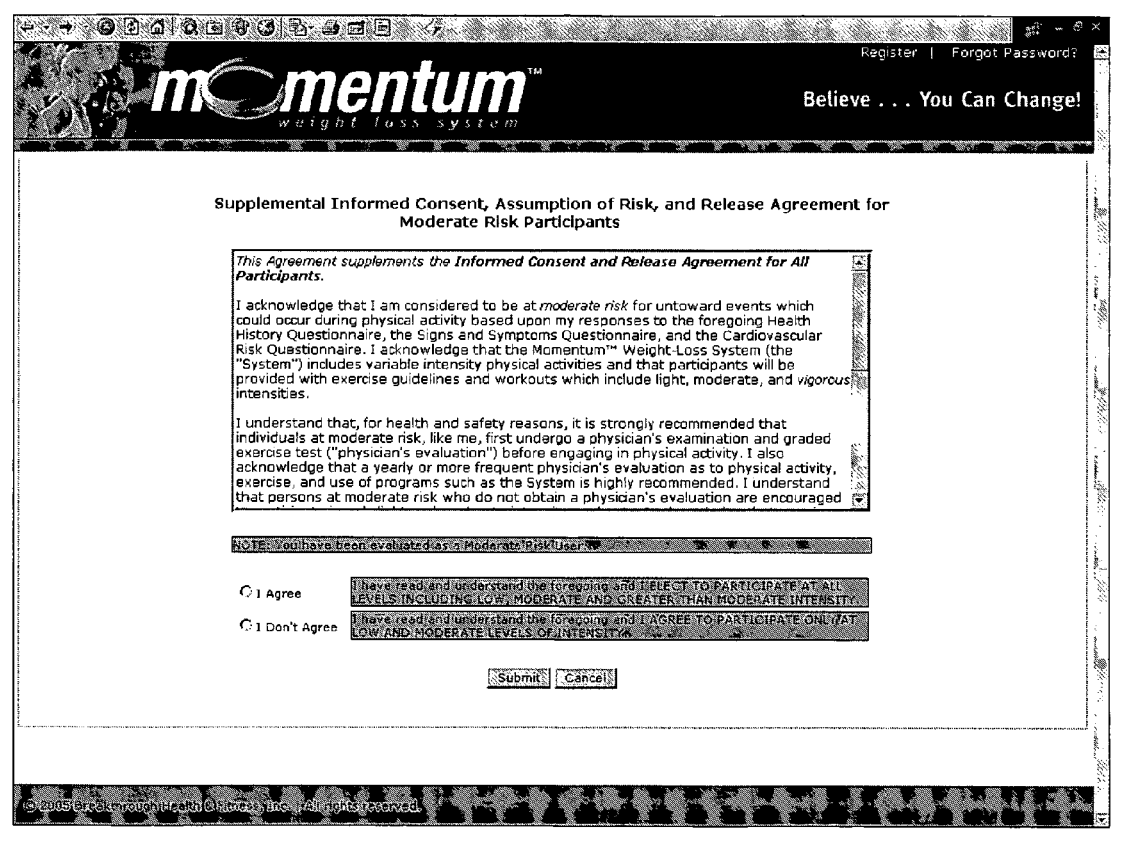

FIG. 8 provides a further, supplemental Informed Consent, Assumption of Risk, and Release Agreement for Moderate Risk Participants (the sixth screen of the CV Risk Questionnaire). As the name suggests it is an additional informed consent for Moderate Risk Participants. That is this screen comes only if the user was identified as Moderate Risk User after the questions, as described in screen 4. Now if the user chooses "I Agree" then the user will be associated with LowRiskMasterPlan that is meant for Low Risk Users and if the user chooses "I Don't Agree" then the user will be associated with ModerateRiskMasterPlan that is meant for Moderate Risk Users. If the user chooses to click Cancel then the system displays a Message Page (Cancel Page) as shown in FIG. 24.

Figure 9:
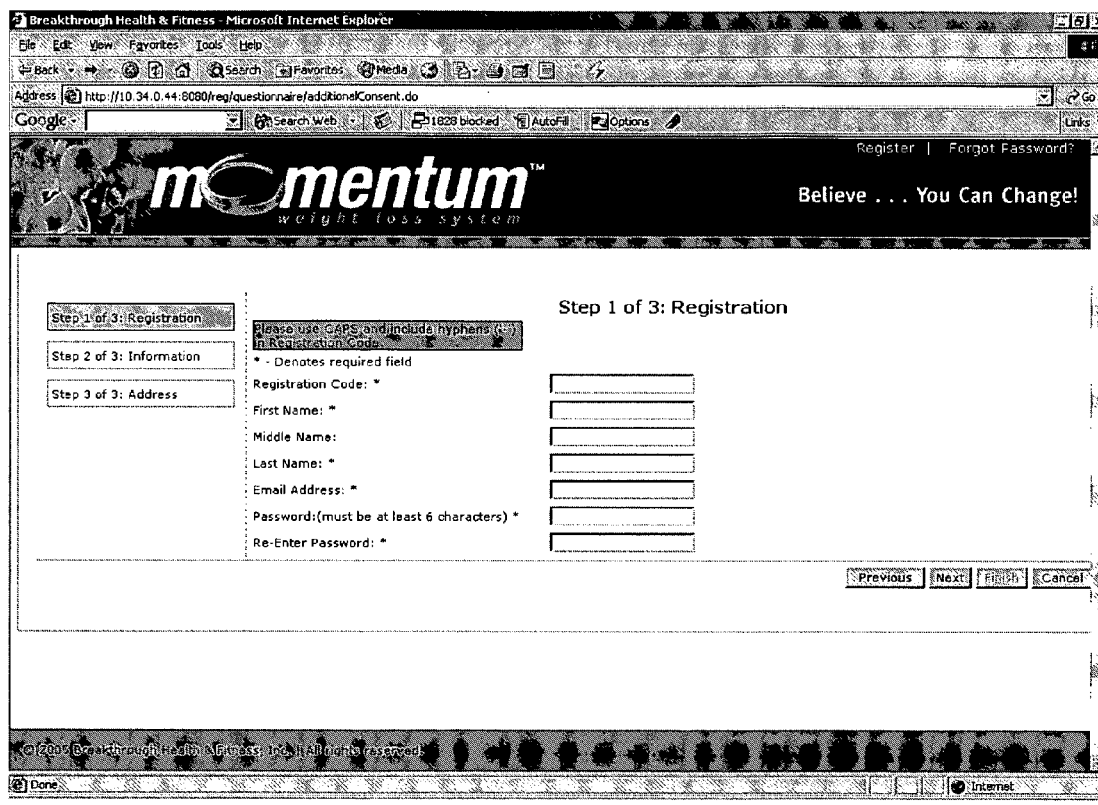
FIG. 9 is one further user interface screen which may be used herewith.

The user who continues may then be directed to a further detailed registration, a part of which being directed to the gathering of information for formulating an appropriate workout regimen for this particular user. FIG. 9 demonstrates a first step, e.g., Step 1 of 3: Registration (Personal Details Screen 1). Once the user has completed the CV Risk Questionnaire, the user may now be directed to enter some personal details. This step 1 of 3 may deal with some information about the account details. Here the user may also be directed to enter the Registration Code that was referred in FIG. 1. User then enters information like First Name, Middle Name, Last Name, Email Address (may include choosing a username for registering into the software.) and a Password. All except Middle Name may be mandatory fields and required input from user. The Registration Code is a unique value (of a secure, predetermined length, and/or may include characters in CAPS and/or hyphens '-' and/or numerals, which could be provided on the inner side of the product box). After entering all and correct data user may be directed to click next to move forward.

Figure 10:
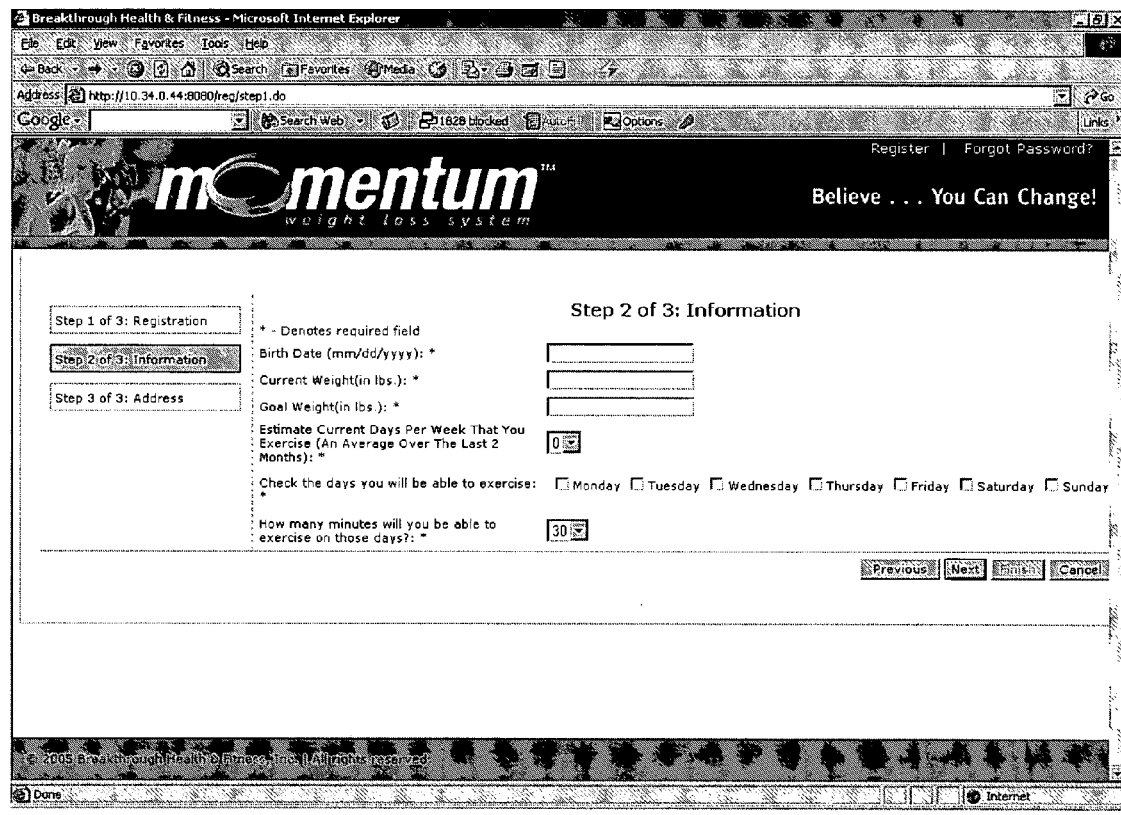
FIG. 10 is still one further user interface screen which may be used herewith.

The next step of the registration process, step 2 of 3 (Personal Details Screen 2) is shown in FIG. 10. This step 2 of 3 provides for obtaining more detailed information about user and his/her workout. Here the user would be required to enter information like Birth Date, Current Weight, and Goal Weight. The user would also set or Select an estimate of Current Days Per Week that user exercises, Days the user will be able to workout and the Duration for the workout(s). It may be that all are designated mandatory fields and require input from user. After entering all and correct data user clicks next to move forward.

Figure 11:
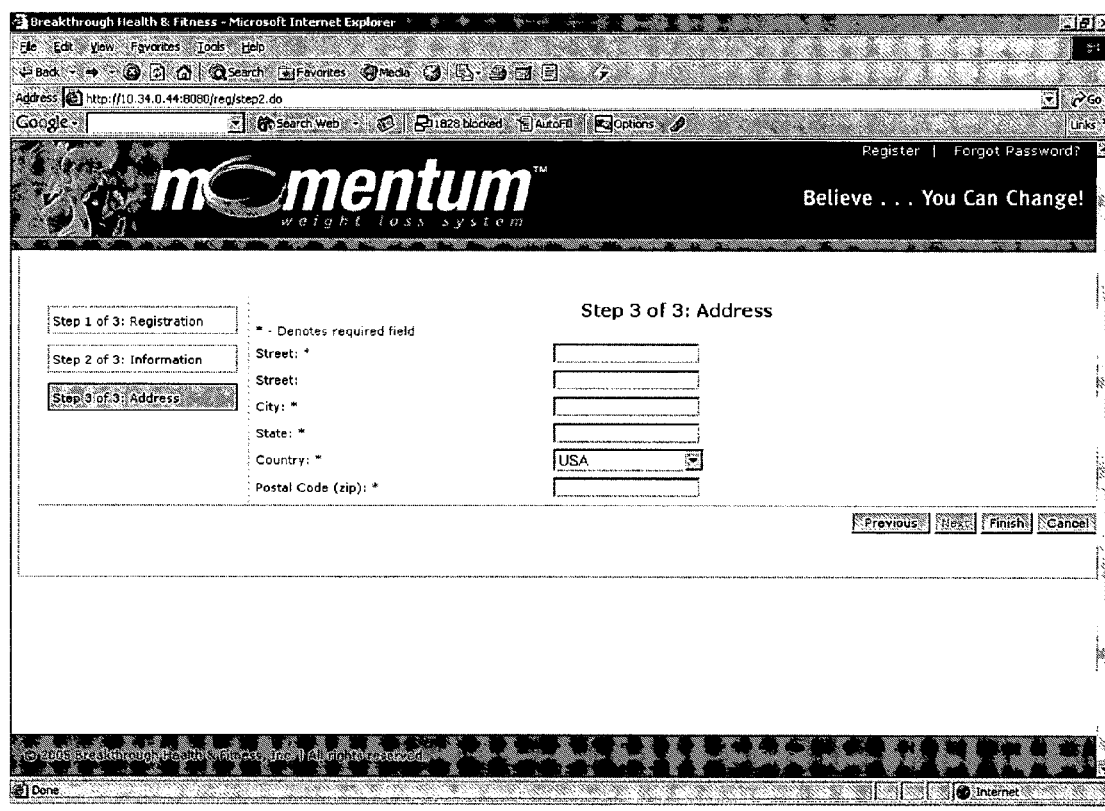
FIG. 11 is yet still one further user interface screen which may be used herewith.

The last step of this exemplar registration process, step 3 of 3: Address (Personal Details Screen 3) is shown in FIG. 11. This step 3 of 3 deals with some contact information about user. Here the user would be required to enter information like Street, City, State and Postal Zip Code. Select Country. Street has two text fields out of which the second is not mandatory and rest all fields are mandatory. After entering all and correct data user clicks Finish to complete Registration Process.

Once the user is through with all the steps all the user information is saved to the Database. Of particular note are some parameters useful in determining appropriate workout regimens. For example the AT (Anaerobic Threshold) is calculated from the newly acquired information according to:

$$AT=(220-age)*0.70 \ \{Moderate\ Risk\ User\}$$

$$AT=(220-age)*0.85 \ \{Low\ Risk\ User\}$$

This AT is then stored with the other user data. Also the risk level of the user is set into the database along with the registration date. This user object is then inserted into the Database. The user may then be taken to the Login page where user can enter his account details supplied at the time of registration and login into the software and check his plan.

Figure 12:
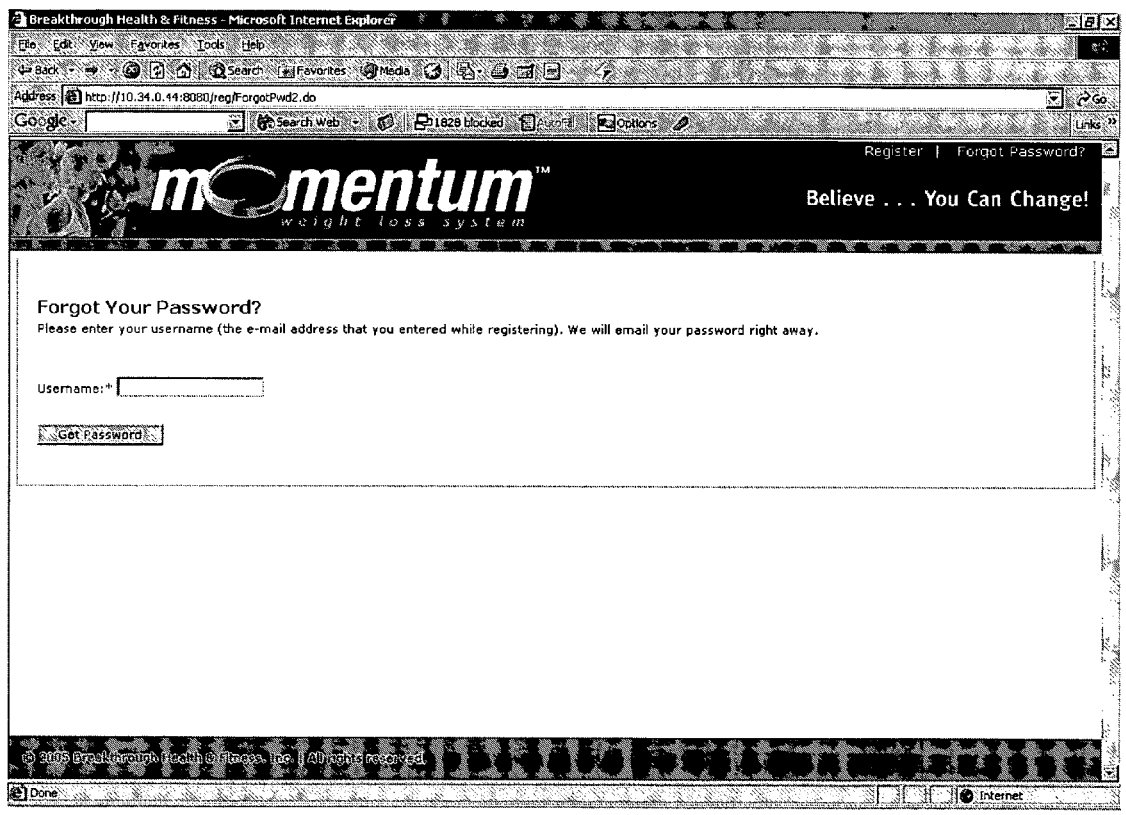
FIG. 12 is another user interface screen which may be used herewith.

A note on a sub-process for a Forgotten Password feature, FIG. 12, which is a facilitation to users who may have forgotten their password for the registered ids. In this sub-process, the User may be directed to enter the email id, which had been supplied at the time of registration. On the click of the button the system may check to determine whether the user is registered, if yes it emails the password to the supplied email address and redirects the system control to the login page. Otherwise, an error message is shown stating that the username supplied is not registered.

Figure 13:
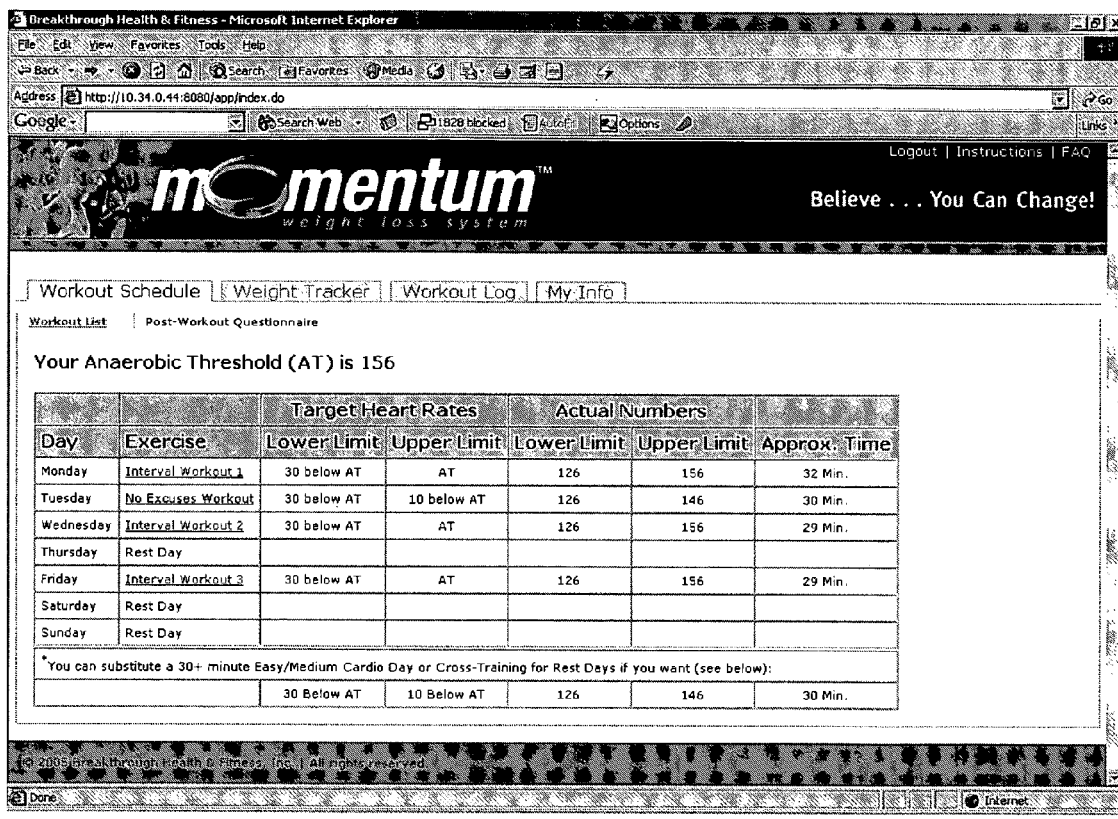
FIG. 13 is yet another user interface screen which may be used herewith.

FIG. 13 sets forth an exemplar first page after entry/registration. The four primary or Major Sections identified above (Workout Schedule; Weight Tracker; Workout Log; and My Info) are shown as tabs along the topside of the display. Shown in more detail is a Workout Schedule, and particularly a Workout List thereof. This may typically be the first screen that comes up after the user logs in after supplying authentic credentials. It may generally display a workout plan, which was made for the user according to the inputs at the time of the Registration process. The pattern of the workout list may/ would be dependent on the number of days selected by the user that they will be available for exercise. Below is a tabular representation, TABLE A, of what a set of workouts the user may directed to have based on the number of days selected.

TABLE A

| Number of Days | Workouts Assigned |
| --- | --- |
| 1 | Interval Workout 1 |
| 2 | Interval Workout 1 on $1^{st}$ day, Interval Workout 2 on the $2^{nd}$ day. |
| 3 | Interval Workout 1 on $1^{st}$ day, No Excuses Workout on $2^{nd}$ day, Interval Workout 2 on $3^{rd}$ day. |
| 4 | Interval Workout 1 on $1^{st}$ day, No Excuses Workout on $2^{nd}$ day, Interval Workout 2 on $3^{rd}$ day, No Excuses Workout on $4^{th}$ day. |
| 5 | Interval Workout 1 on $1^{st}$ day, No Excuses Workout on $2^{nd}$ day, Interval Workout 2 on $3^{rd}$ day, No Excuses Workout on $4^{th}$ day, Interval Workout 3 on 5 day. |
| 6 | Interval Workout 1 on $1^{st}$ day, No Excuses Workout on $2^{nd}$ day, Interval Workout 2 on $3^{rd}$ day, No Excuses Workout on $4^{th}$ day, Interval Workout 3 on $5^{th}$ day, No Excuses Workout on $6^{th}$ day. |
| 7 | Same as 6, because minimum of one day has to be rest day. |

In many implementations, the exercise column may have links to description of exercises set for that particular day.

Figure 14:
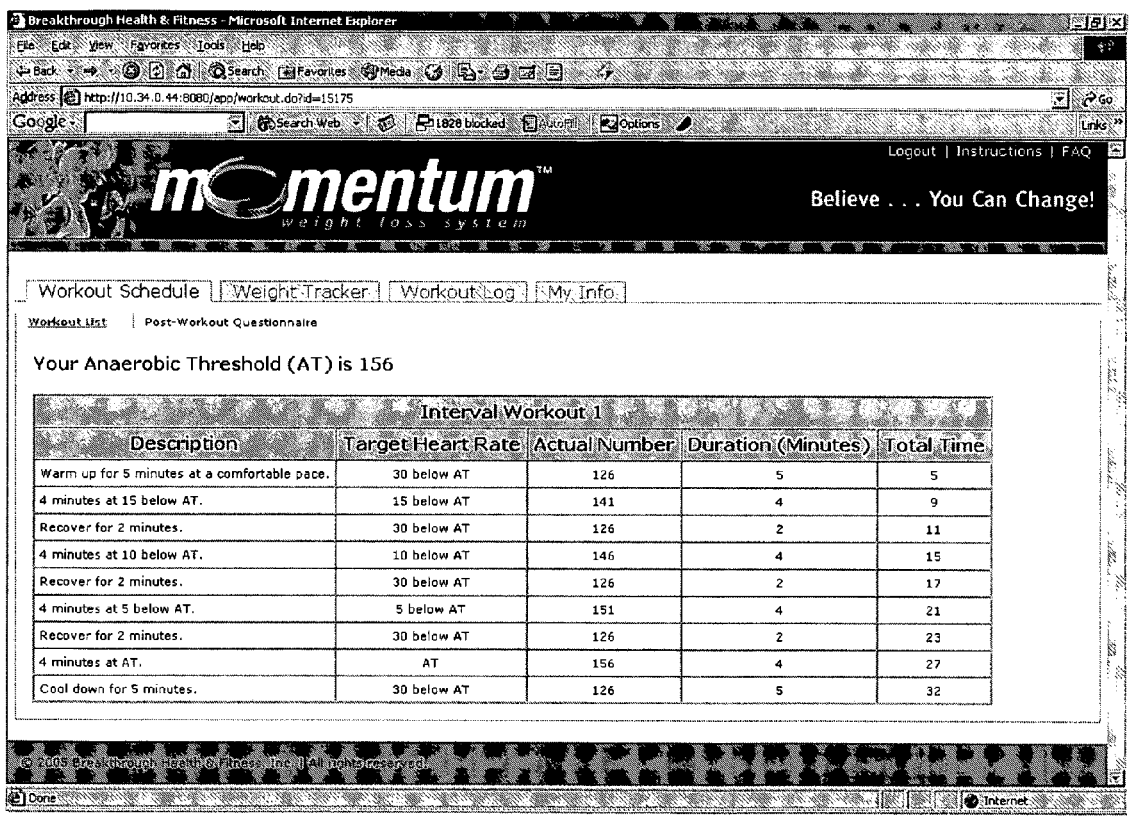
FIG. 14 is still another user interface screen which may be used herewith.
Figure 15:
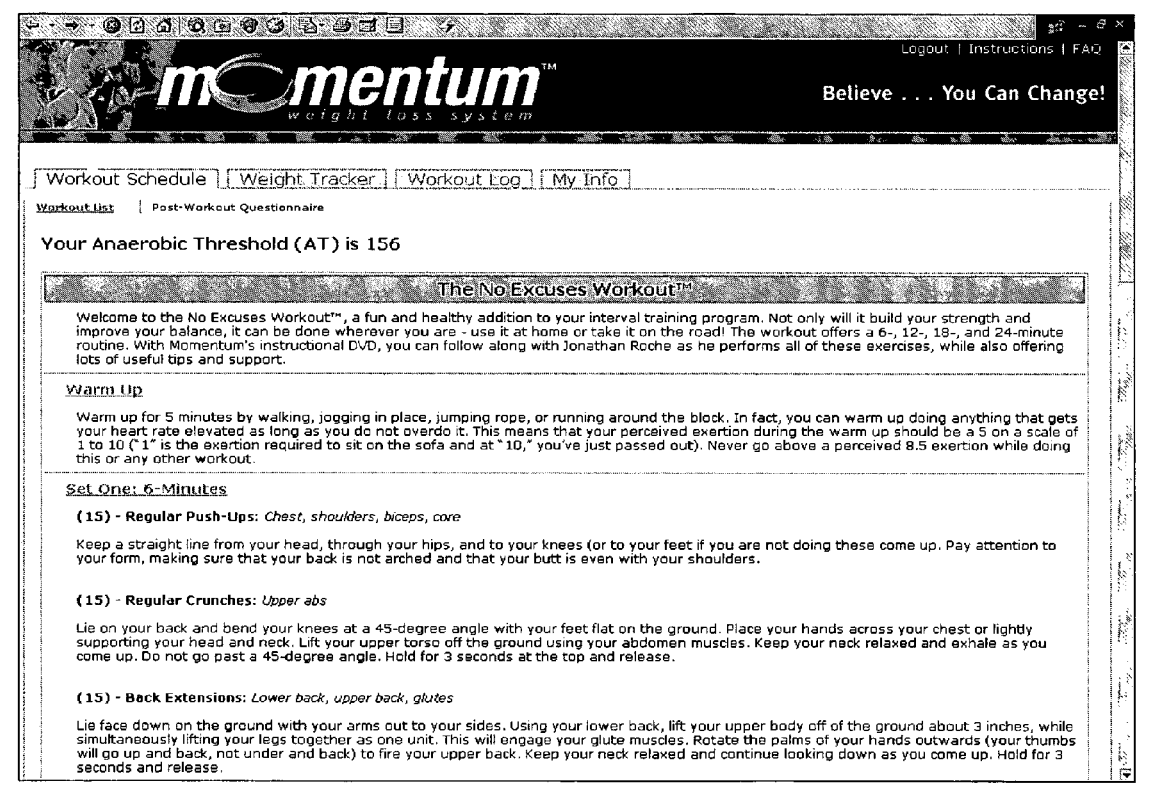

FIG. 14 shows an Interval Workout (1/2/3) which includes exercises planned for particular durations in the displayed plan. FIG. 15 presents an alternative No Excuses Workout.

Figure 16:
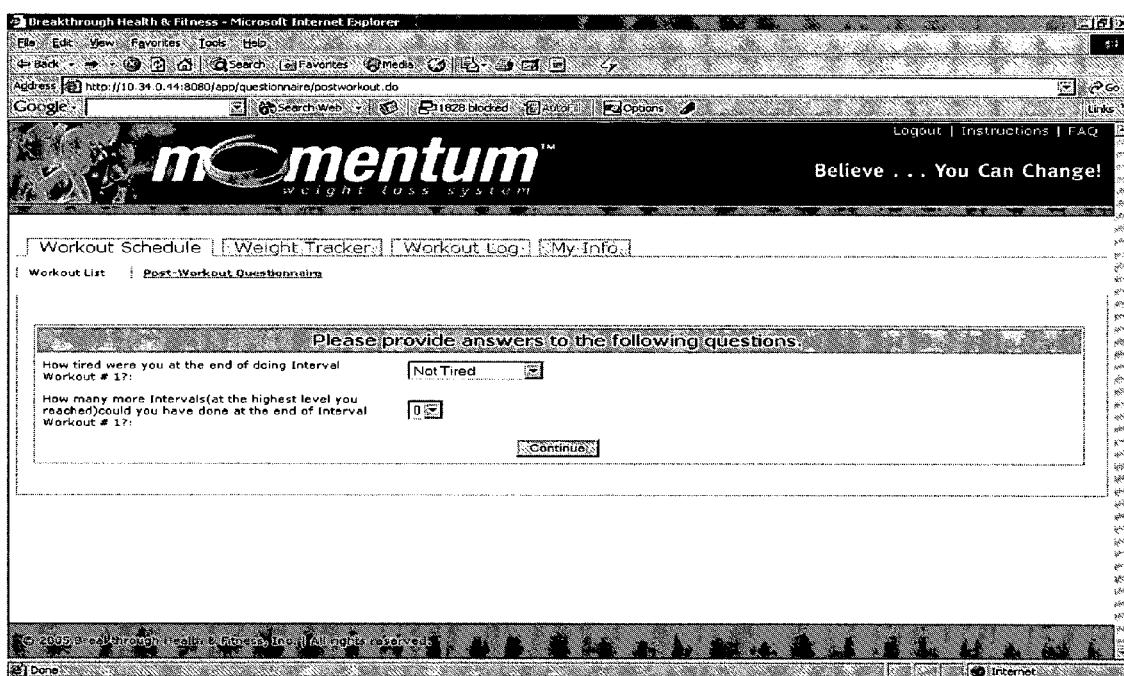
FIG. 16 is a further user interface screen which may be used herewith.

FIG. 16 presents a Post-Workout Questionnaire as an alternative sub-section of the Workout Schedule. Here the user may be directed to give answers to a few questions, such as how tired or how many more intervals the user was or could perform, and accordingly the AT of the User may be adjusted.

Figure 17:
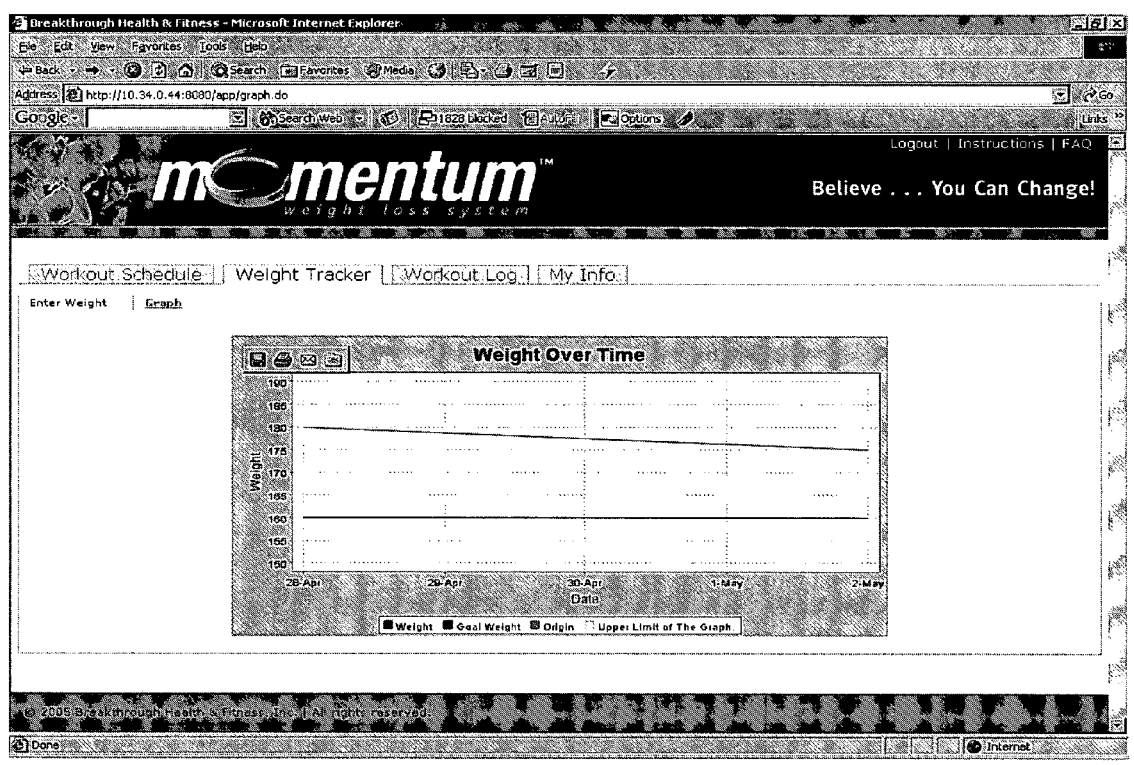
FIG. 17 is a still further user interface screen which may be used herewith.
Figure 18:
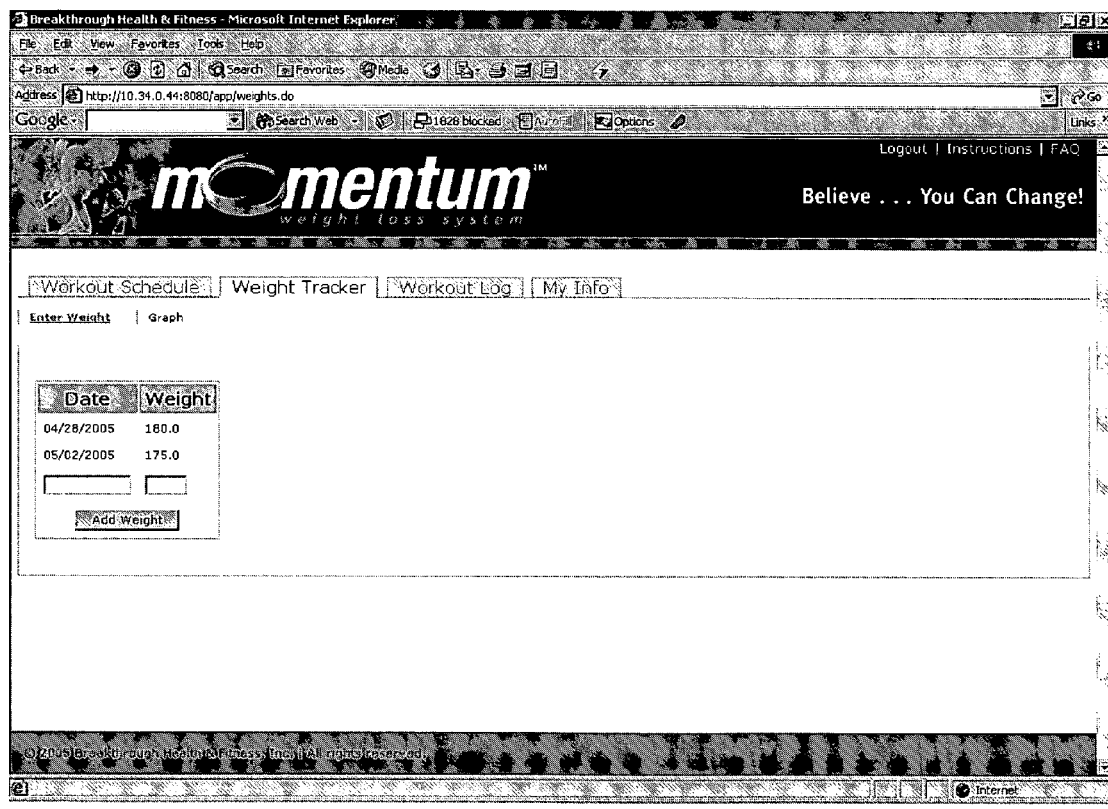
FIG. 18 is yet still a further user interface screen which may be used herewith.

In a second of the major sections, FIG. 17 provides a view of a Weight Tracker functionality, here shown using a Graphical form. It is a graphical representation of the statistics of the weight of a user over time. Thus letting the user have a picture of his/her transition after subsequent workouts. The graph may have a lower limit set below the Goal Weight of the User (Origin) and Upper limit above the weight at registration time (Upper Limit of the Graph). But this screen may be dependent on the Enter Weight screen, the graph only showing up when a user has entered data at least once after he/she has registered. FIG. 18 provides a user interface screen for entering weight for use by the weight tracker; where the user can enter his/her weight after a regular time period interval, so as to keep a record of his data and also to help generate the graph of the transition, as shown in previous screen. In some implementations, it may be desirable to set the date of weight entered having to be within a certain period of the current day (as for example within two weeks before current day).

Figure 19:
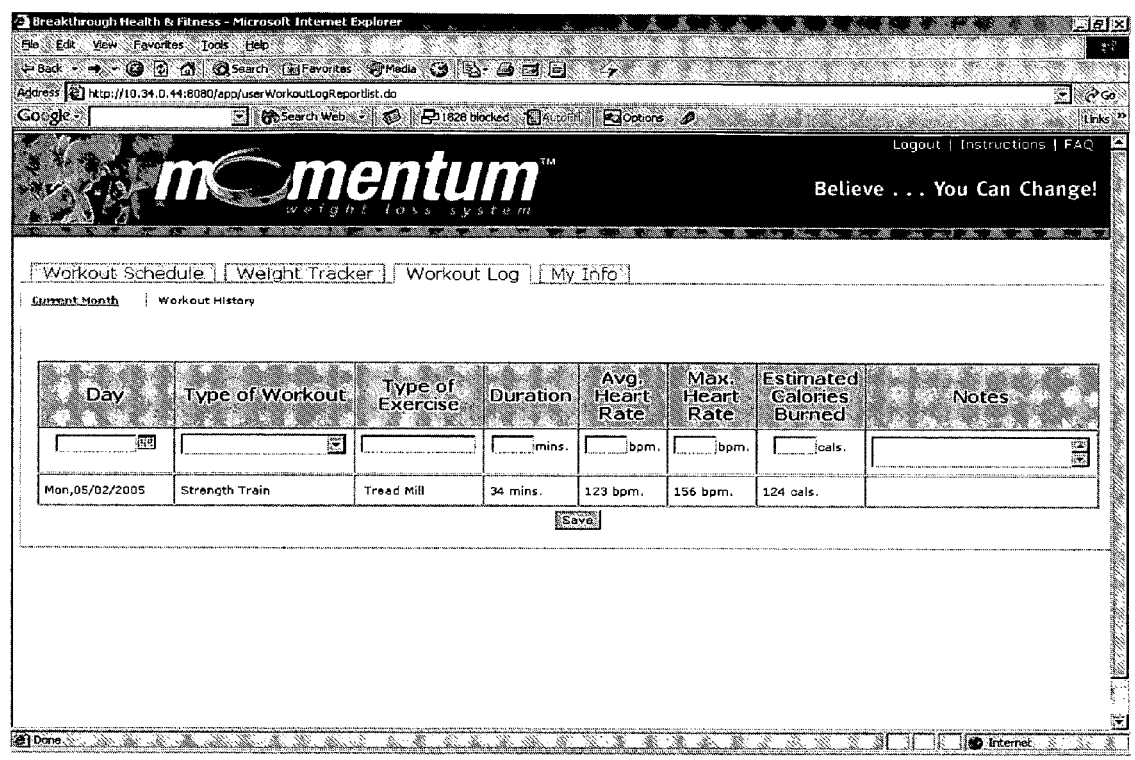
FIG. 19 is one further user interface screen which may be used herewith.
Figure 20:
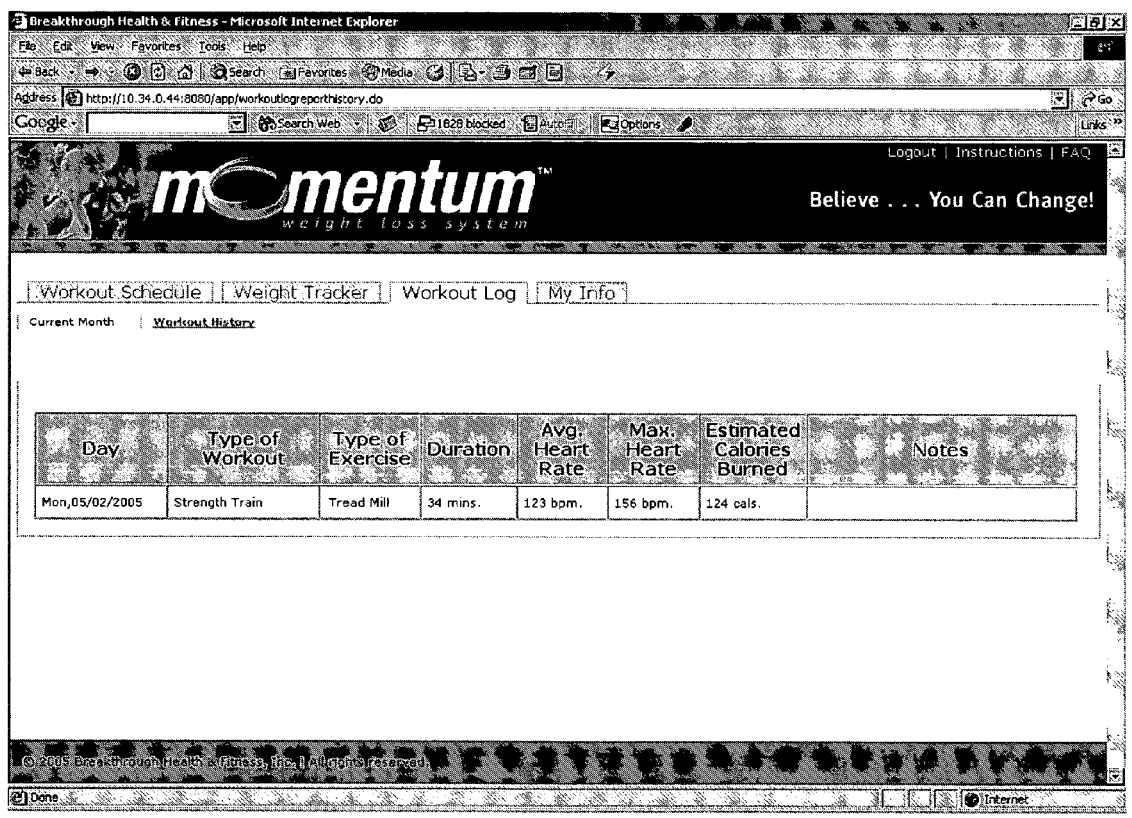
FIG. 20 is still one further user interface screen which may be used herewith.

FIG. 19 presents a third of the major sections shown on the principal screens; namely, a Workout Log, as for the current month (or other period). The current month page gives the user a user interface (UI) to enter details such as the Date, Type of Workout, Type of Exercise, Duration, Avg. Heart Rate, Max Heart Rate, Estimated Calories (Cal.) Burnt and Notes (if any), along with, displaying corresponding rows of data pertaining to date in current month. It may be set that when the user comes on this screen for the first time after registering and he/she hasn't entered any record yet he/she will get a message that "No Workouts have been entered for this Month ". It may also be pre-established that here the user can only enter data for dates up to and including (less than or equal to) current day.

FIG. 20 depicts a second sub-section of the Workout Log here referred to as a Workout History. The workout history page may give the user a report of his/her workout details such as the Date, Type of Workout, Type of Exercise, Duration, Avg. Heart Rate, Max Heart Rate, Estimated Cal. Burnt and Notes (if any), up to the current date.

Figure 21:
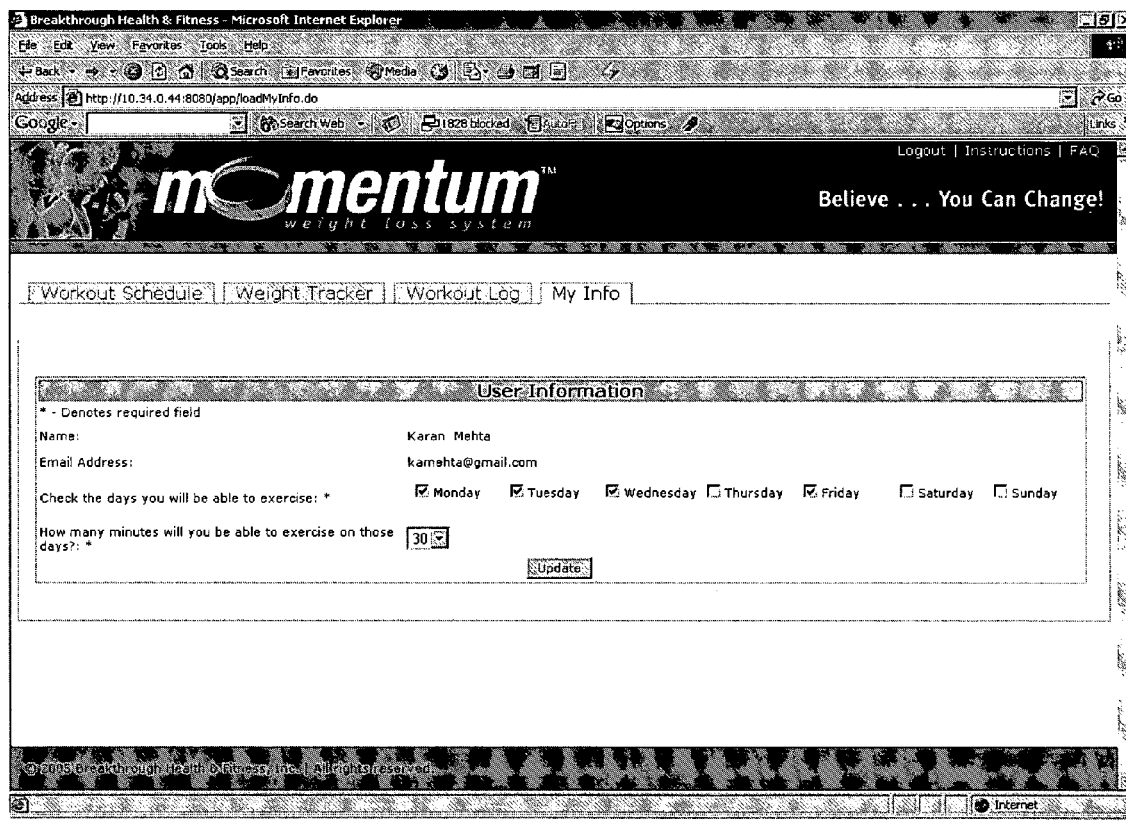
FIG. 21 is still one further user interface screen which may be used herewith.

FIG. 21 presents a fourth of the major sections shown on the principal screens; namely, a My Info page which may enable the user to view, and edit some of his/her details that are required for updating the workout plan i.e. The Days for workout and the Hours he/she will be able to exercise per day. Both fields may be set as mandatory and not to be left blank by the user. On submission of the data user details can be updated and the workout plan can be changed accordingly, displaying a message to user that the user's requested changes have been made. Clicking on the Workout Schedule tab can validate the same. Other details may be changed here, such as "Your Address Details", "Your Goal Weight" and "Your Language Preference".

Figure 22:
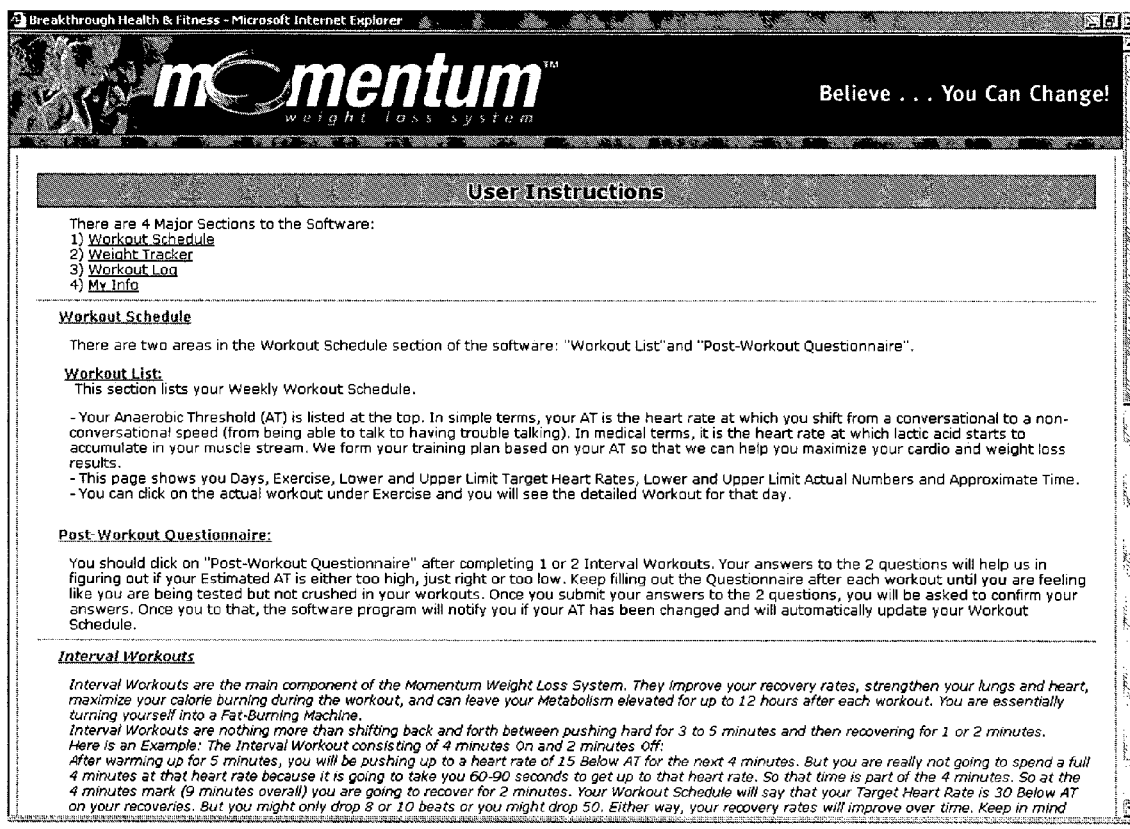
FIG. 22 is still one further user interface screen which may be used herewith.

FIG. 22 provides a sample Instructions page. This may be a normal help page that opens a new window and facilitates users in understanding the application better. This can be accessed after the user has logged in by clicking the Instructions Link in a particular location, as for example at the top right corner of every page. FIG. 23 is a FAQ (frequently asked questions) page which may be a normal question and answer (Q & A) page that opens a new window and answers most of the queries that users can have while using the software. This can be accessed after the user has logged in by clicking the FAQ Link in a particular location, as for example in the top right corner of every page.

FIG. 24 presents a Cancel Page which may be used to cancel out of the program at any point. FIG. 25 presents a High Risk User Refund Page. Utilities herefor have been introduced above.

An overview of still other features of the program whether in software or otherwise: 1) A user may be notified when he or she has not input workouts or weight in the prior two weeks—This may occur automatically as through e-mail or other electronic or other means; 2) A points program may be used wherein a user will receive points for logging in workout and weight loss results and for referring new users to the system. The points may then be redeemable for rewards/prizes which may include workout gear, gym bags, sunglasses, etc. As the customer base grows, so will the range of the products available through the points program; 3) Weight Loss Challenges: a feature may be included that enables users to set up weight loss challenges with friends, co-workers, family, anyone; they just need to be users of the program hereof (referral points from the points program may be used to pay off here). The software may include and/or create a web site (really an area for the participants to log on and see how everyone is doing) to track the challenge throughout the pre-determined challenge period; 4) Customized Motivation Music MP3s: Users may be provided the ability to pick the music and the amount of time they want to workout and then have the software create MP3 workouts (with the system and/or a personal trainer guiding the users through a live or recorded highly effective interval workout) based on the user's available time.

The points program may also be referred to as a Rewards program (e.g., a Rewards™ program) (see e.g., FIG. 26) which may be designed to help the user maintain a consistent workout schedule—the best way to maximize fitness and health results. Earning Points may be a simple process—the user simply working out and then recording the results. The System would then, preferably automatically, add and tally the user's points. The point tally can then be checked and Points redeemed for free or reduced merchandise by visiting the Rewards page. The user can earn Points in one or more ways, such as the following three ways: Recording workout data on the Workout Log Page; Tracking weight on the Weight Tracker Page; and/or Refer new users to the Momentum Fitness & Weight Loss System.

The Recording of workout data on the Workout Log Page may be worth a certain number of points (as for example, 5 POINTS; perhaps even a maximum of 5 Points per Monday through Sunday week). The user would then, after exercise with the System, record results on the Workout Log Page on the personal Web software. The user may then receive 5 Points per week when entering results into the Workout Log. Although it may be recommended that the user record data for every workout to fully track your exercise results, it may be established that the user need only to record data for one workout per week to earn the maximum of 5 points. Note also, it may be established that the user may enter data for up to 2 weeks of workouts at one time to earn Points. This would make it so that a user would not be able to back-date the workout data for more than 14 days. The user may be limited to receiving the maximum 5 points for each of these two back-dated weeks.

The Tracking of weight on the Weight Tracker Page may be worth a certain number of points (as for example, 5 POINTS; perhaps even a maximum of 5 Points per Monday through Sunday week). The user may then Record his/her weight each week on the Weight Tracker Page on the personal Momentum Web software. The user would then receive 5 Points per week when entering results into the Weight Tracker. The user may be free to enter weight as many times as wished during the week—earning a maximum of points (e.g., 5 points) whether updating weight 1 or 7 times per week. Note it may also be established that a user may enter data for up to 2 weeks of weight data at one time to earn Points. This may mean that a user would not be able to back-date weight data for more than 14 days, the user receiving the maximum 5 points for each of these two back-dated weeks.

The Referring of new users to the Fitness & Weight Loss System may involve variations on points received. In one instance, where the user may Purchase additional Fitness & Weight Loss Systems for your family and friends, this may be worth a premium of points (e.g., 50 POINTS; perhaps with no maximum Points). In an alternative, when a user's friends or family members purchase the Fitness & Weight Loss System through the website, the user may earn a maximum number of points (again, e.g., 50 Points). The new customer would just need to enter the referral name when asked during checkout. It may be noted that it may be established to have a limit or to have no limit to the amount of points a user can earn when purchasing additional Momentum Systems or when a user refers new customers to the system.

Figure 27:
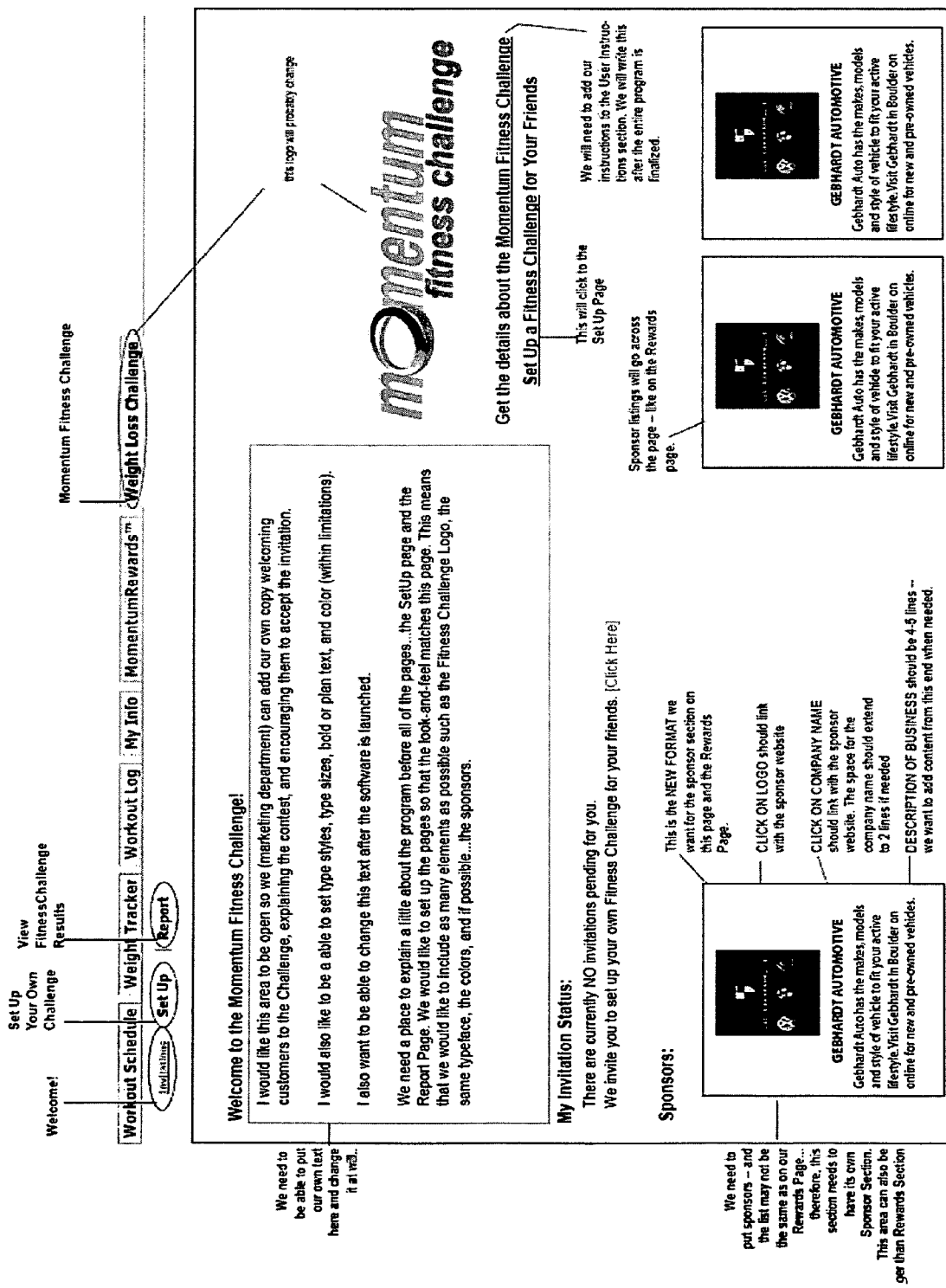
FIG. 27 is still one further user interface screen which may be used herewith.

FIG. 27 provides a view of a Momentum Fitness Challenge Template for use herewith. This part of the software methodology and/or system will enable users to set up fitness and/or weight loss challenges with their friends, family, co-workers, wedding party or strangers. The creator/user specifies what will be tracked—workouts and/or weight loss—and then other people are invited by e-mail to participate. The invitees must be or become customers to participate in the challenge. The participants can then track the status of the challenge through their software.

Figure 28:
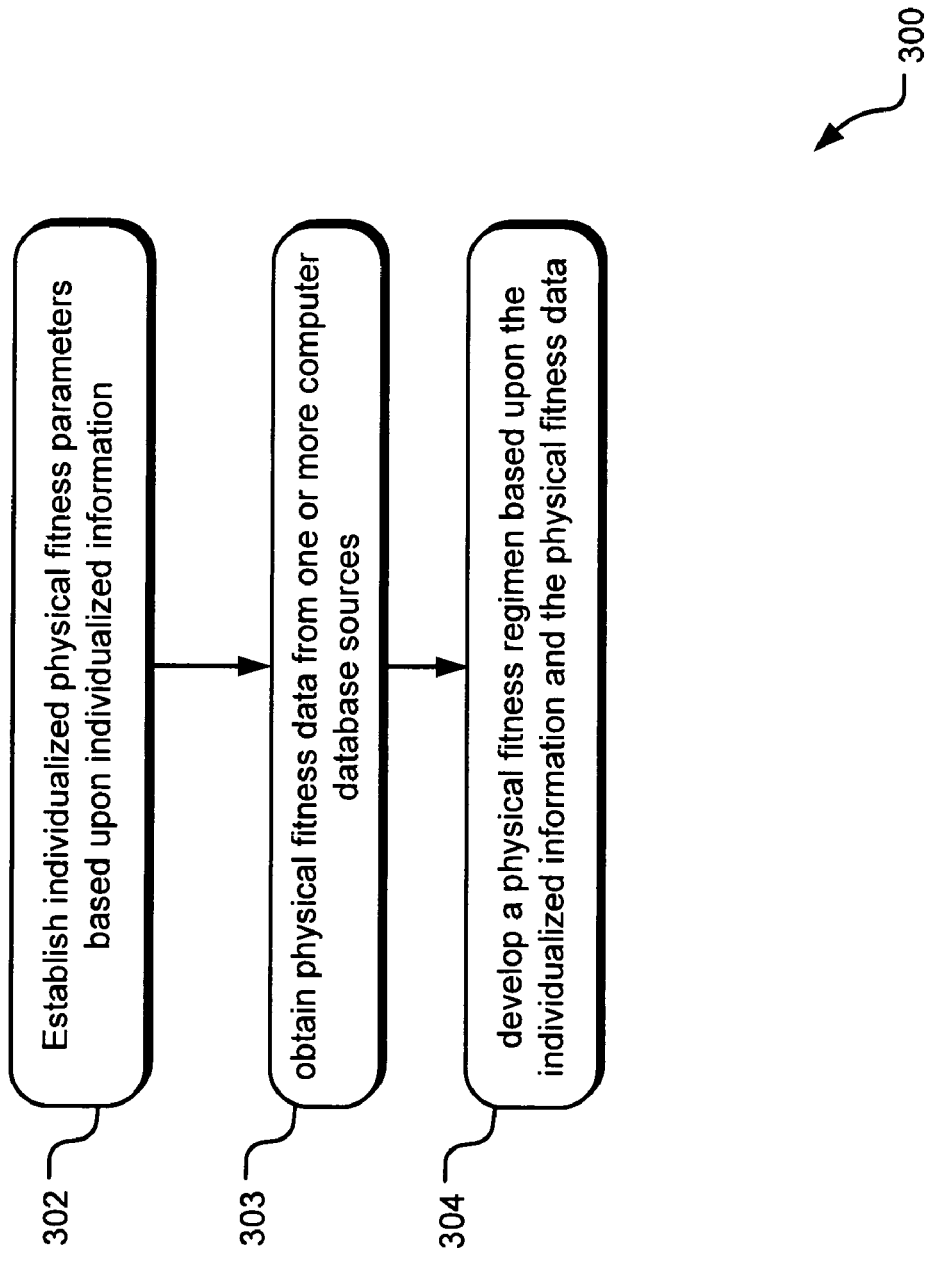
FIG. 28 is a schematic flow chart of a method hereof.

FIG. 28 provides a flow of method 300 hereof, particularly one which may be a computer-implemented method, for developing a physical fitness regimen, the method generally including; establishing individualized physical fitness parameters based upon individualized information (operation 302); obtaining physical fitness data from one or more computer database sources (operation 303); and, developing a physical fitness regimen based upon the individualized information and the physical fitness data (operation 304). The method may further include optimizing the physical fitness regimen; and/or establishing the parameters as one of baseline goals or intermediately changed goals; and/or wherein the developing includes calculating an AT; and/or includes including interval training. The method may further include using a user interface having at least a display portion; particularly in some instances wherein the display portion includes a display of a workout regimen. It may alternatively further include receiving user input information; and/or wherein the user input information includes information to increase comfort level of the user.

Figure 29:
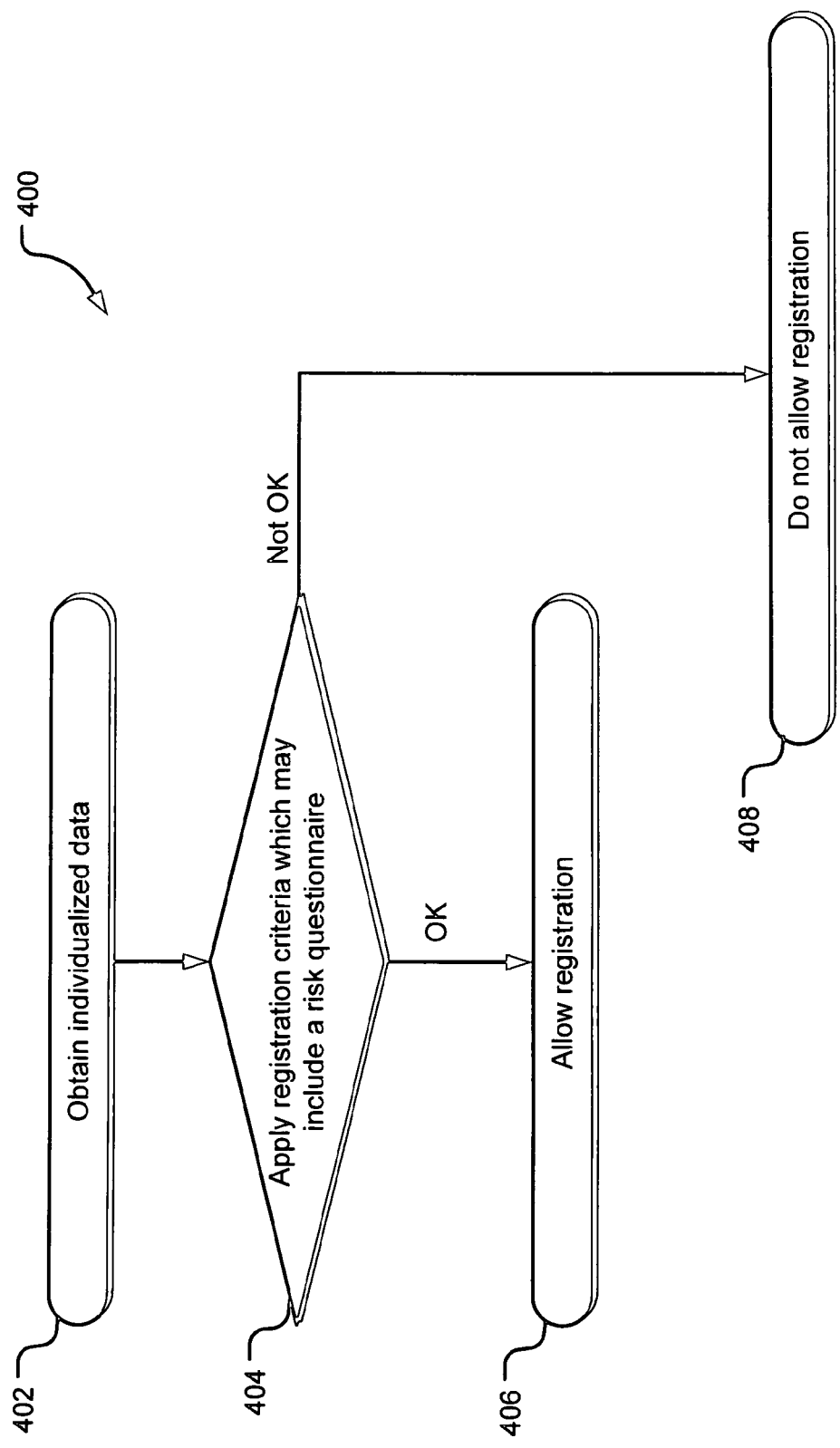
FIG. 29 is another schematic flow chart of a method hereof.

FIG. 29 provides an alternative flow 400 wherein the user may be screened from registering if they don't have or meet sufficient health minimums. In a first step, the system obtains information (operation 402). Then, the system may make a determination of meeting threshold minimums (operation 404). If sufficient, the user will be allowed to register (operation 406), but, if not, then the user may be re-directed, and not allowed to register (operation 408). A variation on this is if the user may be categorized in an intermediate level where they may be allowed to register if they accept a full waiver of any liability to the operator of the system.

In some implementations, articles of manufacture are provided as computer program products. One implementation of a computer program product provides a computer program storage medium readable by a computer system and encoding a computer program. Another implementation of a computer program product may be provided in a computer data signal embodied in a carrier wave by a computing system and encoding the computer program.

Figure 30:
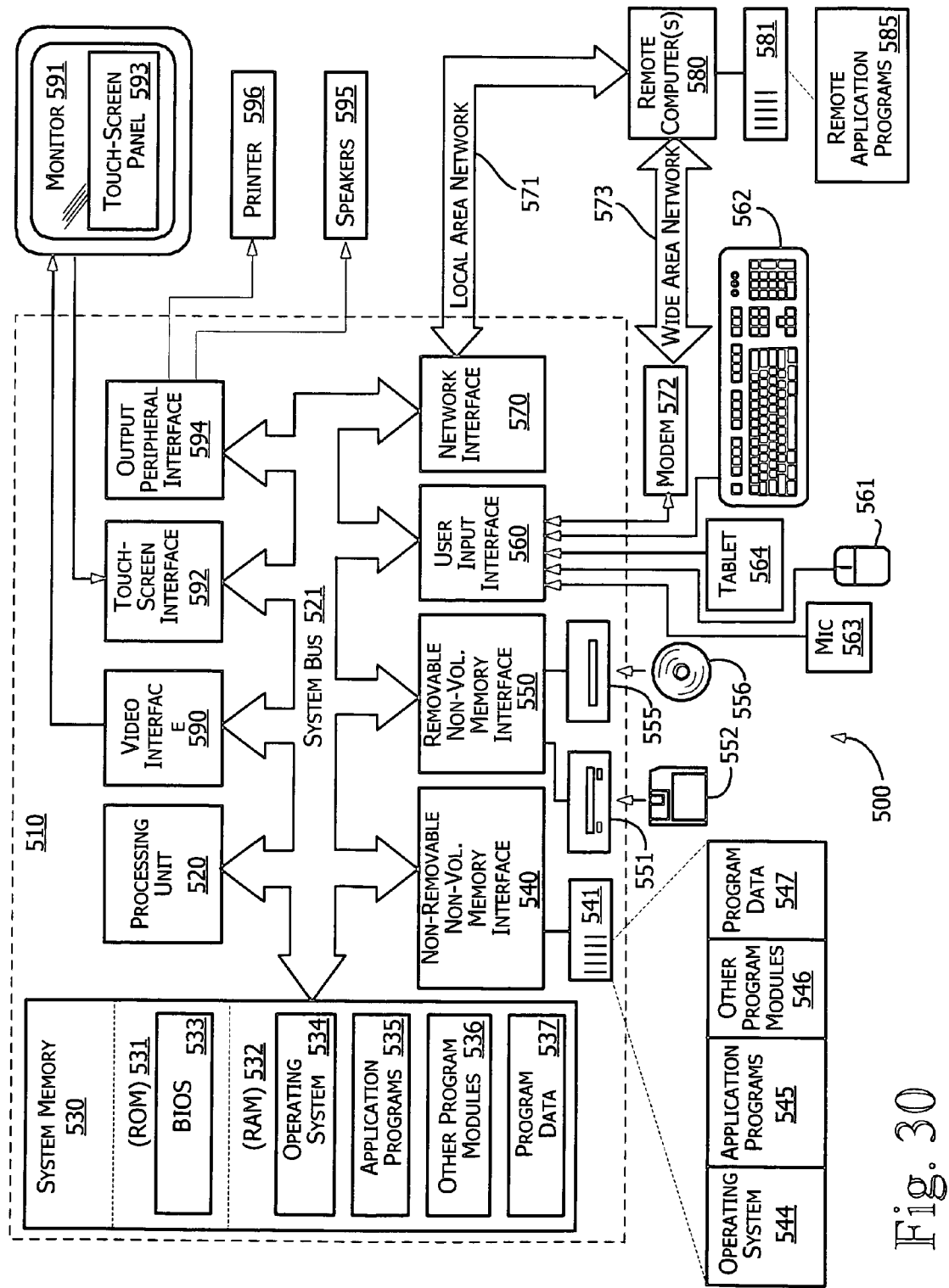
FIG. 30 is a schematic representation of one or more computer systems which may be used herewith.

Example hardware and an operating environment are shown in FIG. 30 for implementing the technology hereof, these including a general purpose computing device in the form of a computer 520, including a processing unit 521, a system memory 522, and a system bus 523 that operatively couples various system components including the system memory to the processing unit 521. There may be only one or there may be more than one processing unit 521, such that the processor of computer 520 comprises a single central-processing unit (CPU), or a plurality of processing units, commonly referred to as a parallel processing environment. The computer 520 may be a conventional computer, a distributed computer, or any other type of computer; the invention is not so limited.

The system bus 523 may be any of several types of bus structures including a memory bus or memory controller, a peripheral bus, a switched fabric, point-to-point connections, and a local bus using any of a variety of bus architectures. The system memory may also be referred to as simply the memory, and includes read only memory (ROM) 524 and random access memory (RAM) 525. A basic input/output system (BIOS) 526, containing the basic routines that help to transfer information between elements within the computer 520, such as during start-up, is stored in ROM 524. The computer 520 further includes a hard disk drive 527 for reading from and writing to a hard disk, not shown, a magnetic disk drive 528 for reading from or writing to a removable magnetic disk 529, and an optical disk drive 530 for reading from or writing to a removable optical disk 531 such as a CD ROM or other optical media.

The hard disk drive 527, magnetic disk drive 528, and optical disk drive 530 are connected to the system bus 523 by a hard disk drive interface 532, a magnetic disk drive interface 533, and an optical disk drive interface 534, respectively. The drives and their associated computer-readable media provide nonvolatile storage of computer-readable instructions, data structures, program modules and other data for the computer 520. It should be appreciated by those skilled in the art that any type of computer-readable media which can store data that is accessible by a computer, such as magnetic cassettes, flash memory cards, digital video disks, random access memories (RAMs), read only memories (ROMs), and the like, may be used in the example operating environment.

A number of program modules may be stored on the hard disk, magnetic disk 529, optical disk 531, ROM 524, or RAM 525, including an operating system 535, one or more application programs 536, other program modules 537, and program data 538. A user may enter commands and information into the personal computer 520 through input devices such as a keyboard 540 and pointing device 542. Other input devices (not shown) may include a microphone, joystick, game pad, satellite dish, scanner, or the like. These and other input devices are often connected to the processing unit 521 through a serial port interface 546 that is coupled to the system bus, but may be connected by other interfaces, such as a parallel port, game port, or a universal serial bus (USB). A monitor 547 or other type of display device is also connected to the system bus 523 via an interface, such as a video adapter 548. In addition to the monitor, computers typically include other peripheral output devices (not shown), such as speakers and printers.

The computer 520 may operate in a networked environment using logical connections to one or more remote computers, such as remote computer 549. These logical connections are achieved by a communication device coupled to or a part of the computer 520; the invention is not limited to a particular type of communications device. The remote computer 549 may be another computer, a server, a router, a network PC, a client, a peer device or other common network node, and typically includes many or all of the elements described above relative to the computer 520, although only a memory storage device 550 has been illustrated in FIG. 30. The logical connections depicted in FIG. 30 include a local-area network (LAN) 551 and a wide-area network (WAN) 552. Such networking environments are commonplace in office networks, enterprise-wide computer networks, intranets and the Internet, which are all types of networks.

When used in a LAN-networking environment, the computer 520 is connected to the local network 551 through a network interface or adapter 553, which is one type of communications device. When used in a WAN-networking environment, the computer 520 typically includes a modem 554, a network adapter, a type of communications device, or any other type of communications device for establishing communications over the wide area network 552. The modem 554, which may be internal or external, is connected to the system bus 523 via the serial port interface 546. In a networked environment, program modules depicted relative to the personal computer 520, or portions thereof, may be stored in the remote memory storage device. It is appreciated that the network connections shown are examples only and other means of and communications devices for establishing a communications link between the computers may be used.

In an example implementation, a establishing module individualized physical fitness parameters, an obtaining physical fitness data module, and a developing of a regimen module, and/or other modules may be incorporated as part of the operating system 535, application programs 536, or other program modules 537. Transaction logs, enlistment records, and other data may be stored as program data 538.

The technology described herein may be implemented as logical operations and/or modules in one or more systems. The logical operations may be implemented (1) as a sequence of processor-implemented steps executing in one or more computer systems and (2) as interconnected machine or circuit modules within one or more computer systems. Likewise, the descriptions of various component modules may be provided in terms of operations executed or effected by the modules. The resulting implementation is a matter of choice, dependent on the performance requirements of the underlying system implementing the described technology. Accordingly, the logical operations making up the embodiments of the technology described herein are referred to variously as operations, steps, objects, or modules. Furthermore, it should be understood that logical operations may be performed in any order, unless explicitly claimed otherwise or a specific order is inherently necessitated by the claim language.

The above specification provides a complete description of the structure and use of example implementations of the presently-described technology. Although various implementations of this technology have been described above with a certain degree of particularity, or with reference to one or more individual implementations, those skilled in the art could make numerous alterations to the disclosed implementations without departing from the spirit or scope of the technology hereof. Since many implementations can be made without departing from the spirit and scope of the presently described technology, the appropriate scope resides in the claims hereinafter appended. In particular, it should be understood that the described technology may be employed in virtually all, if not indeed, all software, firmware and/or hardware environments however these may exist. Other implementations are therefore contemplated. Furthermore, it should be understood that any operations may be performed in any order, unless explicitly claimed otherwise or a specific order is inherently necessitated by the claim language. It is intended that all matter contained in the above description and shown in the accompanying drawings shall be interpreted as illustrative only of particular implementations and are not limiting to the embodiments shown. Changes in detail, methodology or structure may be made without departing from the basic elements of the present technology as defined in the following claims

The invention claimed is:

1. An assembly for physical fitness comprising;
   a computer system for recording input data, calculating optimized parameters and developing a potentially variable physical fitness regimen;
   data input hardware connected to the computer system, the data input hardware providing for inputting to the computer system individualized physical fitness parameters based upon data specific to an individual;
   database download hardware connected to the computer system for downloading general non-individualized physical fitness data from one or more computer database sources;
   physical fitness data gathering hardware adapted to be connected to the computer system for gathering personal physical fitness data from an individual executing or having executed a physical training exercise, and downloading the physical fitness data to the computer system;
   the computer system configured to generate a program code for an individualized physical fitness interval training regimen, the interval training regimen involving a training event during which there is a shifting back and forth between pushing hard for a period, and then recovering for another period, the interval training regimen being based upon the individualized information and the non-individualized and personal physical fitness data.

2. An assembly according to claim 1 wherein the physical fitness regimen is optimized from one or more of the individualized physical fitness parameters, general non-individualized physical fitness data, and personal physical fitness data.

3. An assembly according to claim 1 wherein the individualized physical fitness parameters are one or both of baseline goals or intermediately changed goals.

4. An assembly according to claim 1 wherein the development of an individualized physical fitness regimen includes calculating an anaerobic threshold or AT for use in developing the individualized physical fitness interval training regimen according to claim 1, the regimen involving shifting back and forth between pushing hard for a period, and then recovering for another period, the interval training regimen being based upon the individualized information and the physical fitness data, including the anaerobic threshold or AT.

5. An assembly according to claim 1 wherein the physical fitness regimen includes a heart-rate based interval training regimen.

6. An assembly according to claim 5 wherein the physical fitness data gathering hardware includes a heart rate monitor adapted to generate heart rate data to be downloaded to the computer system by one or both of manual or automatic processes.

7. An assembly according to claim 6 wherein the computer system further includes a user interface having at least a display portion, and the display portion includes a display of a workout regimen.

8. An assembly according to claim 1 wherein the physical fitness data gathering hardware further includes hardware for receiving user input information.

9. An assembly according to claim 8 wherein the user input information includes information to increase comfort level of the user.

10. A computer program product encoding a computer program for a computer process that executes on a computer system for developing a physical fitness regimen, the computer process comprising:

establishing individualized physical fitness parameters based upon data specific to an individual;

obtaining general, non individualized physical fitness data from one or more computer database sources;

gathering personal physical fitness data from an individual executing or having executed a physical training exercise, and developing a program code for an individualized physical fitness interval training regimen, the regimen involving shifting back and forth between pushing hard for a period, and then recovering for another period, the interval training regimen being based upon the individualized information and the physical fitness data.

11. A computer program product according to claim 10 wherein the computer system is one or both of a personal computer and a web-based computer system.

12. A computer program product according to claim 10 wherein the physical fitness regimen is optimized.

13. A computer program product according to claim 10 wherein the parameters are one of baseline goals or intermediately changed goals.

14. A computer program product according to claim 10 wherein the developing of an individualized physical fitness interval training regimen includes calculating an AT for use in developing the individualized physical fitness interval training regimen, the regimen involving shifting back and forth between pushing hard for a period, and then recovering for another period, the interval training regimen being based upon the individualized information and the physical fitness data, including the anaerobic threshold or AT.

15. A computer program product according to claim 10 wherein the developing includes a heart-rate based interval training regimen, and wherein the computer system includes a heart rate monitor adapted to generate heart rate data to be downloaded to the computer system by one or both of manual or automatic processes.

16. A computer program product according to claim 10 further including a user interface having at least a display portion.

17. A computer program product according to claim 16 wherein the display portion includes a display of a workout regimen.

18. A computer program product according to claim 17 further including receiving user input information.

19. A computer program product according to claim 18 wherein the user input information includes information to increase the comfort level of the user.

20. A computer assembly for physical fitness comprising;

a computer for recording input data, calculating optimized parameters and developing a potentially variable physical fitness regimen;

data input hardware connected to the computer system, the data input hardware including one or more of hardware for manually or vocally inputting data, and the data input hardware providing for inputting to the computer system individualized physical fitness parameters based upon data specific to an individual;

physical fitness data gathering hardware adapted to be connected to the computer system for gathering personal physical fitness data from an individual executing or having executed a physical training exercise, and downloading the physical fitness data to the computer system;

the computer configured to generate a program code for an individualized physical fitness interval training regimen, the interval training regimen involving a training event during which there is a shifting back and forth between pushing hard for a period, and then recovering for another period, the interval training regimen being based upon the individualized information and the personal physical fitness data.

* * * * *